US010987056B2

(12) United States Patent
Sasazawa

(10) Patent No.: US 10,987,056 B2
(45) Date of Patent: Apr. 27, 2021

(54) MEDICAL INSTRUMENT AND FIXING TOOL

(71) Applicant: TERUMO KABUSHIKI KAISHA, Tokyo (JP)

(72) Inventor: Shuhei Sasazawa, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 85 days.

(21) Appl. No.: 16/277,971

(22) Filed: Feb. 15, 2019

(65) Prior Publication Data

US 2019/0175108 A1 Jun. 13, 2019

Related U.S. Application Data

(63) Continuation of application No. PCT/JP2017/024143, filed on Jun. 30, 2017.

(30) Foreign Application Priority Data

Aug. 26, 2016 (JP) .............................. JP2016-165935

(51) Int. Cl.
*A61M 5/00* (2006.01)
*A61B 5/00* (2006.01)
*A61B 5/1473* (2006.01)
*A61B 5/145* (2006.01)
*A61M 5/142* (2006.01)

(52) U.S. Cl.
CPC .......... *A61B 5/6833* (2013.01); *A61B 5/1473* (2013.01); *A61B 5/14532* (2013.01); *A61M 5/00* (2013.01); *A61M 5/14248* (2013.01); *A61B 2560/0412* (2013.01); *A61M 5/14212* (2013.01); *A61M 2205/3576* (2013.01)

(58) Field of Classification Search
CPC ......... A61B 2560/0412; A61B 5/6833; A61M 5/14248
See application file for complete search history.

(56) References Cited

U.S. PATENT DOCUMENTS

| 5,879,373 A | 3/1999 | Roper et al. |
|---|---|---|
| 2004/0236248 A1 | 11/2004 | Svedman |
| 2006/0020192 A1 | 1/2006 | Brister et al. |

(Continued)

FOREIGN PATENT DOCUMENTS

| CN | 104768450 A | 7/2015 |
|---|---|---|
| CN | 108471959 A | 8/2018 |

(Continued)

OTHER PUBLICATIONS

Extended European Search Report dated Dec. 3, 2019 for corresponding European Patent Application No. 17843205.0.

(Continued)

*Primary Examiner* — Christine H Matthews
(74) *Attorney, Agent, or Firm* — Foley & Lardner LLP

(57) ABSTRACT

A medical instrument includes: a medical device; a sheet type attaching member having an attachment surface that is attachable to a subject; and a fixing tool fixing the medical device to the attaching member. The fixing tool includes: a first engaging member located on the medical device; and a second engaging member located on a side of the attaching member opposite the attachment surface, the second engaging member being engageable with the first engaging member by rotation of the first engaging member with respect to the second engaging member.

6 Claims, 15 Drawing Sheets

(56) References Cited

U.S. PATENT DOCUMENTS

2010/0204657 A1    8/2010  Yodfat et al.
2012/0277696 A1   11/2012  Gonzalez-Zugasti et al.

FOREIGN PATENT DOCUMENTS

| EP | 0 063 333 A2 | 10/1982 |
| EP | 3 195 795 A1 | 7/2017 |
| JP | S56-44890 Y2 | 10/1981 |
| JP | 2010-534085 A | 11/2010 |
| JP | 5102350 B2 | 12/2012 |
| JP | 2013-010029 A | 1/2013 |
| JP | 2014-516645 A | 7/2014 |
| WO | WO-2010/140687 A1 | 12/2010 |
| WO | WO-2011/076871 A1 | 6/2011 |

OTHER PUBLICATIONS

Translation of the Written Opinion of the International Searching Authority in corresponding application No. PCT/JP2017/024143.
International Searching Authority, "International Search Report", issued in connection with International Patent Application No. PCT/JP2017/024143, dated Sep. 19, 2017.
International Searching Authority, "Written Opinion," issued in connection with International Patent Application No. PCT/JP2017/024143, dated Sep. 19, 2017.
Office Action dated Sep. 2, 20120 in corresponding Chinese Patent Application No. 201780021017.7.

MEDICAL INSTRUMENT AND FIXING TOOL

CROSS-REFERENCE TO RELATED APPLICATIONS

This is a bypass continuation of PCT Application No. PCT/JP2017/024143, filed on Jun. 30, 2017, which claims priority to Japanese Application No. 2016-165935, filed on Aug. 26, 2016. The contents of these application are hereby incorporated by reference in their entireties.

BACKGROUND

The present disclosure relates to a medical instrument and a fixing tool.

According to the related art, it is known to use a medical instrument attached to skin of a subject when a subject continuously uses the medical instrument for a period of several days to several weeks. For example, Japanese Patent No. 5102350 discloses a case in which a delivery device for delivering a fluid, such as a liquid medicine, is attached to the skin of a subject to thereby be used.

SUMMARY

In the case of attaching a medical instrument to a subject over a period of several days to several weeks, in order to prevent the attached medical instrument from falling off the skin of the subject, it is preferable to attach the medical instrument to the subject using a tape with a strong adhesive force. Meanwhile, in the case of attaching the medical instrument to the subject using the tape with a strong adhesive force, it is more likely to apply a strong stimulation to the skin when the medical instrument is detached from the skin due to termination of use of the medical instrument or the like. That is, as the adhesive force of the tape is increased, detachment of the medical instrument from the skin becomes difficult, such that at the time of detaching the medical instrument from the skin, the skin may become reddish or the skin may be peeled off. Further, when the medical instrument is detached from the skin, the subject is more likely to feel pain.

An object of the present disclosure is to provide a medical instrument and a fixing tool capable of decreasing pain at the time of detaching the medical instrument from the skin while securing adhesive strength between the medical instrument and the skin.

According to one embodiment, a medical instrument includes: a medical device; a sheet type attaching member having an attachment surface to be attached to a subject; and a fixing tool fixing the medical device to the attaching member, wherein the fixing tool includes: a first engaging member provided on the medical device; and a second engaging member provided on an fixing surface of the attaching member different from the attachment surface, the second engaging member being engageable with the first engaging member by rotation with respect to the first engaging member.

In one aspect, the first and second engaging members come in contact with each other to constitute a rotation axis of rotation, one of the first and second engaging members includes an engagement protrusion part extending in a diameter direction around the rotation axis, and the other includes an engagement receiving part engageable with the engagement protrusion part.

In one aspect, the second engaging member includes: a support part supporting the first engaging member to constitute the rotation axis; and the engagement receiving part provided on the fixing surface to be spaced apart from the support part.

In one aspect, a plurality of pairs of the engagement protrusion part and the engagement receiving part engaged with each other are provided, and each of the pairs of the engagement protrusion part and the engagement receiving part has a shape, size and position, at least one of which is different from that of the other pairs.

In one aspect, the first engaging member includes the engagement protrusion part, and at least one of the first and second engaging members includes an energizing part provided separately from the engagement protrusion part and the engagement receiving part, the at least one of the first and second engaging members being contracted when being pushed toward the other of the first and second engaging members and biasing the engagement protrusion part in a direction opposite to a direction in which the attaching member is positioned to thereby allow the engagement protrusion part to come in contact with the engagement receiving part.

In one aspect, the first engaging member includes the engagement protrusion part and an energizing part connecting the engagement protrusion part and the medical device to each other, and the energizing part is contracted when being pushed toward the second engaging member and energizing the engagement protrusion part in a direction in which the attaching member is positioned to thereby allow the engagement protrusion part to come in contact with the engagement receiving part.

In one aspect, the engagement protrusion part is formed by being pushed toward the other of the first and second engaging members.

In one aspect, one of the first and second engaging members includes a male screw part, and the other includes a female screw part screwable with the male screw part.

According to another embodiment, a fixing tool includes: a first engaging member installable on a medical device; and a second engaging member installable on an fixing surface of sheet type an attaching member having an attachment surface to be attached to a subject, the fixing surface being different from the attachment surface, second engaging member being engageable with the first engaging member by rotation with respect to the first engaging member.

With a medical instrument and a fixing tool according to the present disclosure, it is possible to alleviate pain at the time of detaching the medical instrument from the skin while securing adhesive strength between the medical instrument and the skin.

DETAILED DESCRIPTION

Figure 1:
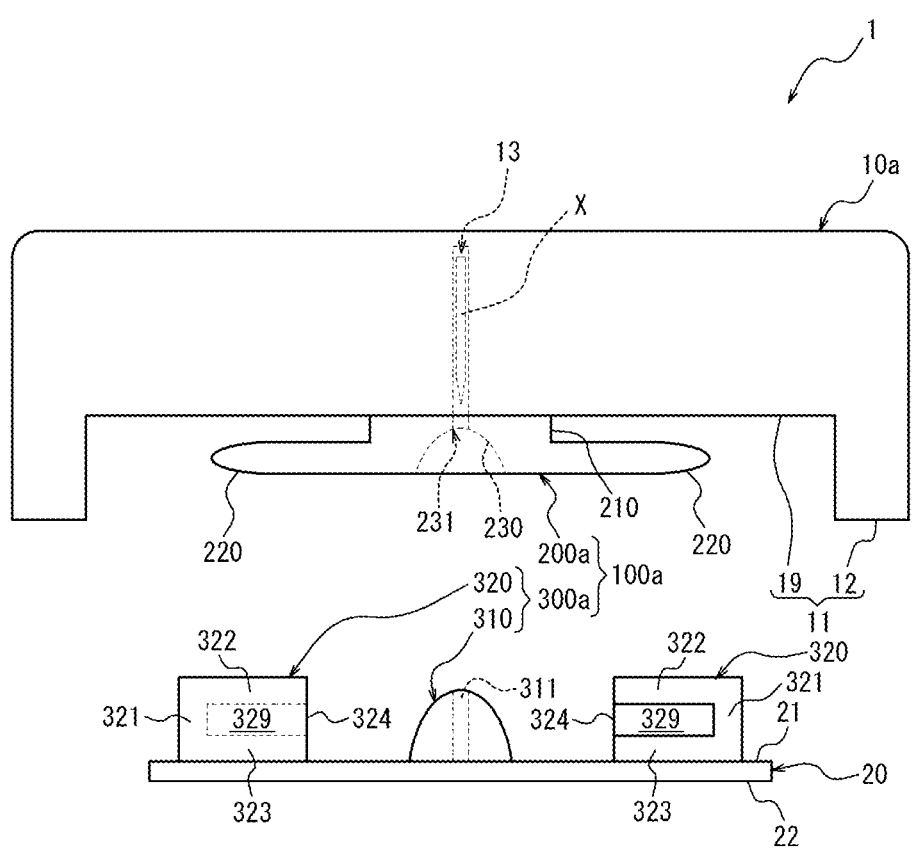
FIG. 1 is a front view of a medical instrument according to a first embodiment of the present invention.

Hereinafter, medical instruments according to embodiments of the present disclosure are described with reference to the accompanying drawings. Common members in respective drawings are denoted by the same reference numerals.

Figure 5:
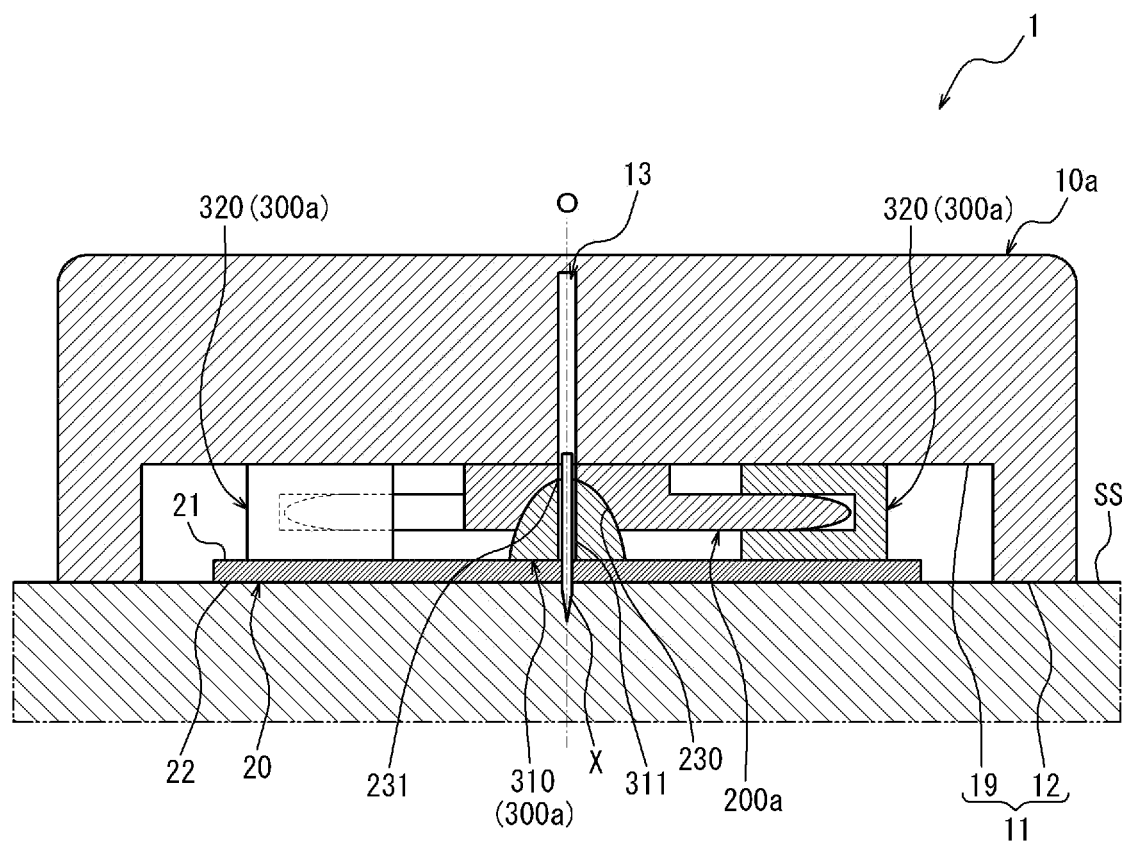
FIG. 5 is a cross-sectional view of the medical instrument illustrated in FIG. 1 during use.

A vertical direction, herein, means a direction perpendicular to a skin surface of a subject when a medical instrument is used for the subject, an upward direction means, for example, an upward direction in FIG. 5, and a downward direction means a direction opposite to the upward direction. Further, a parallel direction means a direction along a plane parallel to the skin surface of the subject when the medical instrument is used for the subject.

First Embodiment

FIG. 1 is a front view of a medical instrument 1 according to a first embodiment of the present invention. As illustrated in FIG. 1, the medical instrument 1 includes a medical device 10a; an attaching member 20; and a fixing tool 100a fixing the medical device 10a to the attaching member 20. The medical instrument 1 illustrated in FIG. 1 is in a state in which the device 10a is not fixed to the attaching member 20 by the fixing tool 100a (hereinafter, appropriately referred to as a "non-fixed state"). The medical instrument 1 is continuously used over a period of about several days to several weeks in a state in which the medical device 10a is fixed to the attaching member 20 by the fixing tool 100a (hereinafter, appropriately referred to as a "fixed state") and the attaching member 20 is attached to the subject, which is equally applied to medical instruments according to other embodiments.

As the medical device 10a, various medical devices can be used depending on objects and uses of the medical instrument 1. For example, the medical device 10a is a measuring device having a control unit continuously measuring biological information of the subject. When the medical device 10a is the measuring device, it is, for example, a measuring device calculating a glucose concentration in subcutaneous tissue by continuous glucose monitoring (CGM). In this case, the subject connects the measuring device to a sensor inserted into the body using a needle-like member X, such as a puncture tool, and attaches the measuring device to the skin to perform CGM. Further, for example, the medical device 10a may be a liquid medicine pump supplying a fluid, such as a liquid medicine, to the body using the same needle-like member X. For example, when the medical device 10a is a liquid medicine pump, the medical device 10a is an insulin pump. The medical device 10a may be another device other than the above-mentioned devices.

The medical device 10a has a bottom surface 11 facing the attaching member 20. In the present embodiment, the bottom surface 11 has a substantially circular shape. Further, a bottom peripheral part 12 positioned at a periphery of the bottom surface 11 protrudes downward more than a bottom central part 19 corresponding to the other region of the bottom surface 11. As the bottom peripheral part 12 protrudes in the downward direction, when the medical instrument 1 is in the fixed state using the fixing tool 100a, the bottom peripheral part 12 covers a periphery of the fixing tool 100a, thereby making it possible to prevent the fixing tool 100a from being exposed to the outside. Hereinafter, for convenience of explanation, in the parallel direction, a horizontal direction in FIG. 1, FIGS. 5 to 7, and FIGS. 10, 12, 13A, 14A, 15, 16A and 17 is simply referred to as a "horizontal direction", and a direction perpendicular to a paper surface in the same drawings is referred to as a "forward and backward direction" in which an inside of the paper surface is a front side and a near side of the paper surface is a rear side. In FIG. 1, for convenience of explanation, illustration of portions of the bottom peripheral part 12 positioned at front and rear ends other than portions thereof positioned at left and right ends of the medical device 10a is omitted and is also appropriately omitted in the following drawings.

The attaching member 20 is a sheet type member and has an fixing surface 21 to which the medical device 10a is fixed by the fixing tool 100a and an attachment surface 22 attached to the skin of the subject. In the present embodiment, the attaching member 20 has a substantially circular shape.

The attaching member 20 can be made of, for example, a rayon non-woven fabric, a polyester non-woven fabric, a polyurethane non-woven fabric, or a plastic based core material (polyethylene, polyester, polyurethane or the like).

An adhesive generating an adhesive force strong enough to attach the attaching member 20 to the skin of the subject is applied onto the attachment surface 22 of the attaching member 20. More specifically, it is preferable that the adhesive force of the attachment surface 22 to the skin is strong enough to allow the medical instrument 1 not to be detached from the skin of the subject for a period of time (for example, several days to several weeks) during which the subject uses the medical instrument 1, and is stronger than that of an ordinary adhesive tape or the like. It is preferable that the attachment surface 22 has an adhesive force to the skin of a degree at which the adhesive force to the skin is constantly maintained for the period during which the subject uses the medical instrument 1 and detachment of the medical instrument 1 from the skin rarely causes pain in the subject.

An area of the attachment surface 22 of the attaching member 20 is smaller than that of the bottom surface 11 of the medical device 10a. Therefore, it is possible to suppress a size (area) of pain felt by the subject when the medical instrument 1 is detached from the skin. Further, when the subject repeatedly uses the medical instrument 1, in view of health, it is not preferable to continuously use the medical instrument 1 at the same site on a skin surface SS (see FIG. 5), but it is easy to change a site of the skin surface SS to be attached by decreasing the area of the attachment surface 22, such that it is possible to suppress the medical instrument 1 from being continuously used at the same site. More specifically, in the present embodiment, when the medical instrument 1 in the fixed state is viewed from above, an outer peripheral contour of the medical device 10a is positioned outside an outer peripheral contour of the attaching member 20.

As an example of the adhesive applied onto the attachment surface 22 of the attaching member 20, a silicone-based adhesive, an acrylic adhesive, or a rubber (natural rubber or synthetic rubber) based adhesive can be used. However, the adhesive is not limited to the adhesives described above. The attachment surface 22 of the attaching member 20 is covered with release paper or the like before the medical instrument 1 is used, and the release paper is peeled off in use.

The fixing tool 100a has a first engaging member 200a provided in the medical device 10a and a second engaging member 300a provided on the fixing surface 21 of the attaching member 20. The fixing tool 100a is a member for allowing the medical instrument 1 in the non-fixed state to be in the fixed state by connecting the medical device 10a and the attaching member 20 to each other.

Figure 2:
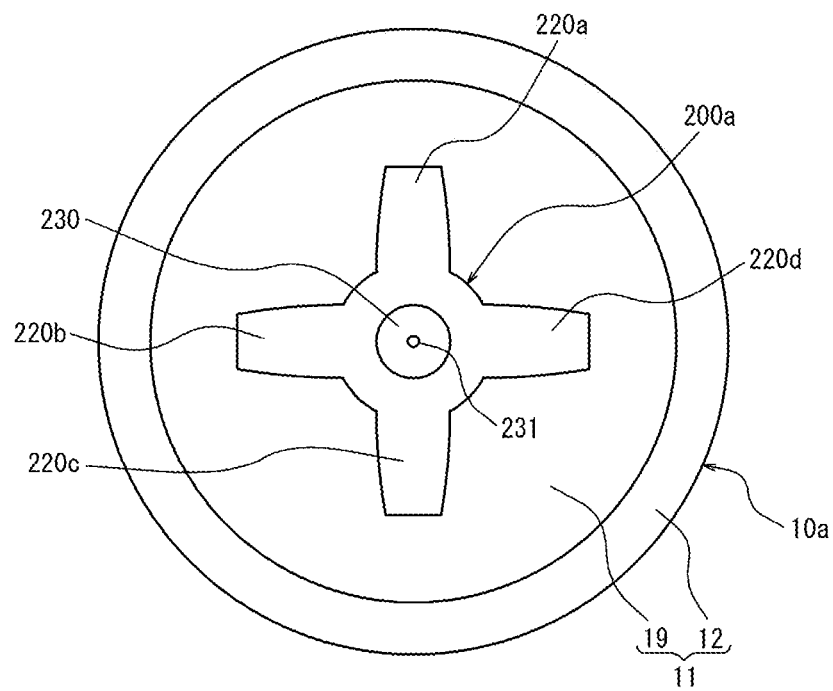
FIG. 2 is a bottom view of a medical device illustrated in FIG. 1.

The first engaging member 200a includes an arm part 210 provided on the bottom central part 19 of the bottom surface 11 of the medical device 10a and extending downwardly from the bottom surface 11 of the medical device 10a; and an engagement protrusion part 220 extending from a lower end of the arm part 210 in the parallel direction, and a central concave part 230 recessed from the lower end of the arm part 210 in the upward direction is formed. In the present embodiment, the first engaging member 200a has four engagement protrusion parts 220. Specifically, the four engagement protrusion parts 220 are four engagement protrusion parts 220a, 220b, 220c and 220d extending in different directions from each other at substantially equal angular intervals based on the central concave part 230 as illustrated in FIG. 2. The four engagement protrusion parts 220 have substantially the same shape and size from each other, respectively. The first engaging member 200a may be formed integrally with the medical device 10a or may be fixed to the medical device 10a by welding or the like. This is equally applied to a first engaging member according to another embodiment to be described below. In FIG. 1, for convenience of explanation, illustration of two engagement protrusion parts 220 extending in the front and rear directions, respectively, is omitted, and is also appropriately omitted in the following drawings.

In the medical device 10a and the first engaging member 200a, a hollow part 13 having an opening part 231 formed in a bottom portion of the central concave part 230 as one end is integrally formed, and the needle-like member X is accommodated in the hollow part 13. In this way, a needle end side of the needle-like member X can partially protrude from the central concave part 230 through the opening part 231.

Examples of a material of the first engaging member 200a can include various resin materials such as: polyethylene, polypropylene, an ethylene-propylene copolymer and other polyolefins; an ethylene-vinyl acetate copolymer (EVA); polyvinyl chloride; polyvinylidene chloride; polystyrene; polyamide; polyimide; polyamideimide; polycarbonate; poly-(4-methylpentene-1); an ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyethylene terephthalate (PET) and other polyesters, polybutylene terephthalate (PBT), polycyclohexane terephthalate (PCT); polyether; polyetherketone (PEK); polyether ether ketone (PEEK); polyether imide; polyacetal (POM); polyphenylene oxide; modified polyphenylene oxide; polysulfone; polyethersulfone; polyphenylene sulfide; polyarylate; aromatic polyester (liquid crystal polymer); polytetrafluoroethylene, polyvinylidene fluoride and other fluorine-containing resins; and the like. Further, a blend or polymer alloy containing one or more of these materials may be used. Examples of the material of the first engaging member 200a may include various glass materials, ceramics materials and metal materials in addition to the above-mentioned materials. The same material can also be used for a first engaging member according to another embodiment to be described below.

The second engaging member 300a is a member engageable with the first engaging member 200a by rotation with respect to the first engaging member 200a and includes a central convex part 310; and an engagement receiving part 320. The central convex part 310 and the engagement receiving part 320 of the second engaging member 300a are disposed at intervals corresponding to the central concave part 230 and the engagement protrusion part 220 of the first engaging member 200a. The central convex part 310 is provided on the fixing surface 21 of the attaching member 20 and protrudes in the upward direction. The central convex part 310 comes in contact with the central concave part 230 of the first engaging member 200a to thereby partially engage with the central concave part 230, thereby making it possible to support the first engaging member 200a, limit linear movement of the first engaging member 200a in the parallel direction and movement of the first engaging member 200a in the downward direction, and enable rotation of the first engaging member 200a along the parallel direction. In other words, the central convex part 310 and the central concave part 230 constitute a rotation axis when the first engaging member 200a rotates with respect to the second engaging member 300a. Further, a passing hole 311 penetrating through the central convex part 310 in the vertical direction is formed in the central convex part 310. The passing hole 311 is in communication with the hollow part 13 at the opening part 231 in a state in which the central convex part 310 comes in contact with the central concave part 230.

Figure 3:
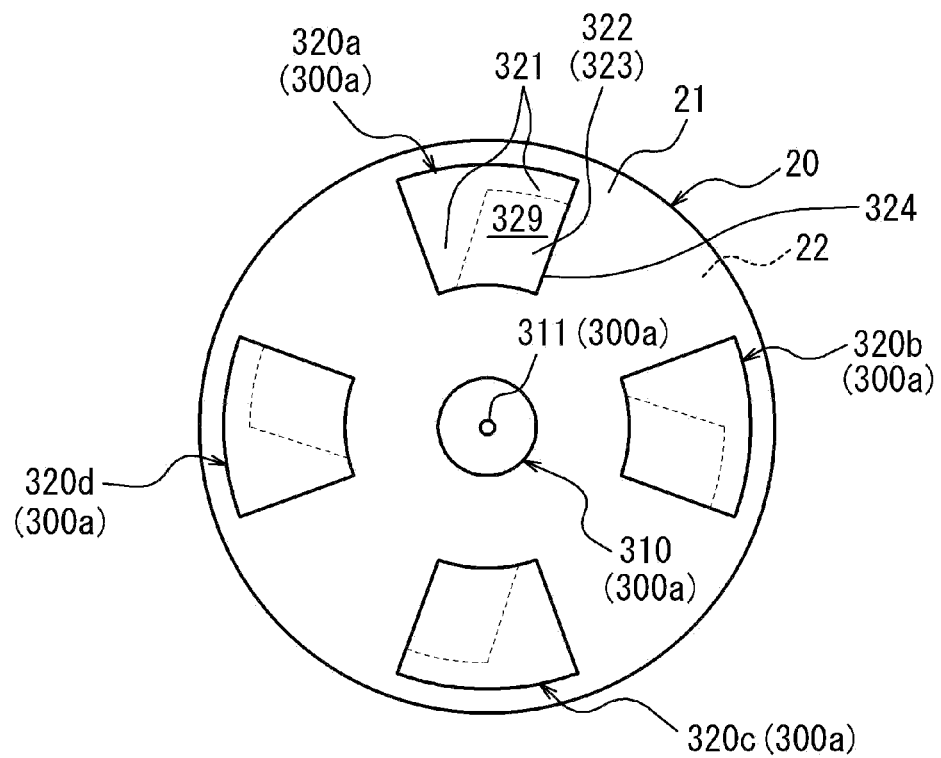
FIG. 3 is a top view of an attaching member illustrated in FIG. 1.

The engagement receiving part 320 is provided on the fixing surface 21 to be spaced apart from the central convex part 310. In the present embodiment, the second engaging member 300a has four engagement receiving parts 320. More specifically, the four engagement receiving parts 320 are engagement receiving parts 320a, 320b, 320c and 320d disposed at substantially equal angular intervals and equal distances based on the central convex part 310 as illustrated in FIG. 3. The four engagement receiving parts 320 have substantially the same shape and size from each other. In FIG. 1, for convenience of explanation, illustration of two engagement receiving parts 320 disposed in the front and rear directions, respectively, is omitted, and is also appropriately omitted in the following drawings.

A hollow part 329 is formed in the engagement receiving part 320 and is in communication with the outside through an opening part 324 formed in a portion of a side surface of the engagement receiving part 320 in the parallel direction. More specifically, the engagement receiving part 320 has a cover part 322 covering an upper portion thereof; a side wall 321 positioned in the periphery in the parallel direction and having the opening part 324 formed therein; and a bottom part 323 covering a lower portion thereof. The hollow part 329 is partitioned by the cover part 322, the side wall 321 and the bottom part 323. In the engagement receiving part 320 according to the present embodiment, the opening part 324 is formed from a surface of the side wall 321 facing the central convex part 310 to a surface positioned on one side (a right-handed side in the present embodiment) in a circumferential direction around the central convex part 310 when viewed in the thickness direction of the attaching member 20 (see FIG. 3). However, a position and a shape of the opening part 324 can be appropriately changed depending on a position and a shape of the engagement protrusion part 220.

The second engaging member 300a is fixed to the attaching member 20, for example, by welding or the like. An area of the fixing surface 21 of the attaching member 20 can be decreased in a range in which the second engaging member 300a can be disposed at the above-mentioned interval. Because the attaching member 20 is the sheet type member, the area of the fixing surface 21 is substantially equal to that of the attachment surface 22. Therefore, in the present embodiment, the area of the attachment surface 22 of the attaching member 20 may also be decreased to be smaller than that of the bottom surface 11 of the medical device 10a in a range in which the second engaging member 300a can be disposed at the fixing surface 21 at the above-mentioned interval, which is preferable in view of improving mountability.

Examples of a material of the second engaging member 300a can include various resin material exemplified as the material of the first engaging member 200a, a blend or polymer alloy containing one or more of these resin materials and the like. It is easy to weld the second engaging member 300a to the attaching member 20 by using these materials, which is preferable. Further, the same material can also be used for a second engaging member according to another embodiment to be described below.

Figure 4A:
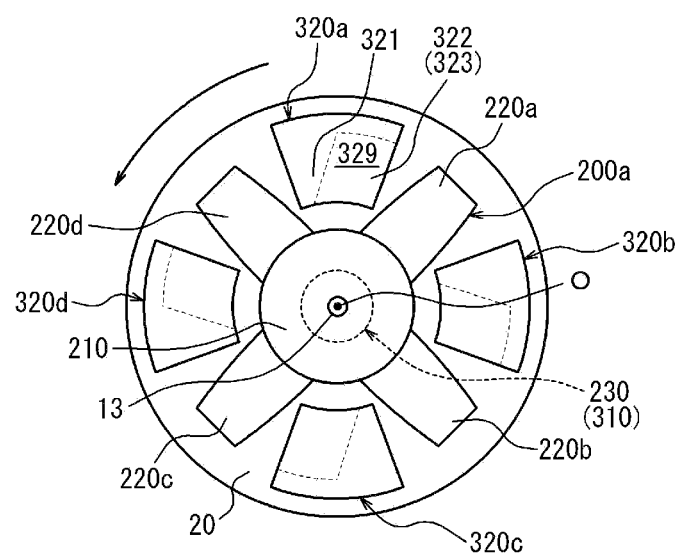
FIGS. 4A and 4B are views illustrating a process of engaging a fixing tool.
Figure 4B:
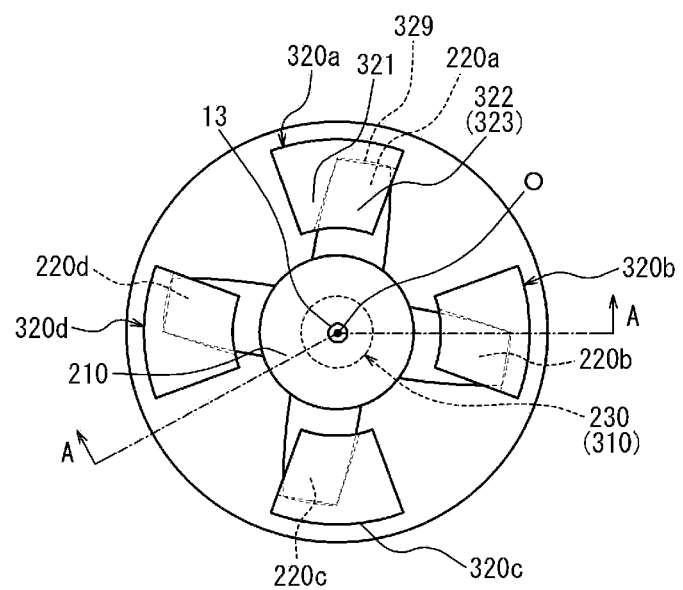

FIGS. 4A and 4B are views illustrating a process of engaging the fixing tool 100a, wherein FIG. 4A illustrates an unengaged state and FIG. 4B illustrates an engaged state. The term "engaged state" means a state in which the first and second engaging members 200a and 300a are engaged with each other, and the term "unengaged state" means a state other than the engaged state. An arrow in FIG. 4A illustrates a direction in which the first engaging member 200a is relatively rotated with respect to the second engaging member 300a at the time of engaging the first and second engaging members 200a and 300a with each other. In FIG. 4, for convenience of explanation, illustration of the medical device 10a is omitted.

As illustrated in FIG. 4A, in the case of installing the first engaging member 200a from above the second engaging member 300a while maintaining a positional relationship in which each of the engagement protrusion parts 220 are disposed between the engagement receiving parts 320, the central concave part 230 comes in contact with the central convex part 310, such that the first engaging member 200a is supported by the central convex part 310. Here, the central convex part 310 and the central concave part 230 serve as a support part and a supported part, respectively, and constitute a rotation axis O in the vertical direction. The first and second engaging members 200a and 300a can rotate around the rotation axis O with respect to each other. Here, the engagement protrusion part 220 is disposed to extend in the diameter direction around the rotation axis O. More specifically, the engagement protrusion part 220 according to the present embodiment is disposed to protrude outwardly from the rotation axis O in the diameter direction.

In the case of rotating the first engaging member 200a with respect to the second engaging member 300a in a left-handed direction (counterclockwise direction) in the state of FIG. 4A, the engagement protrusion part 220 passes through the opening part 324 of the engagement receiving part 320 to thereby be accommodated in the hollow part 329 as illustrated in FIG. 4B. Further, the engagement protrusion part 220 comes in contact with the side wall 321 of the engagement receiving part 320 installed on a rotation path (a left side wall 321 of the engagement receiving part 320 as viewed from the rotation axis O), such that rotation is blocked. Here, movement of the engagement protrusion part 220 in the vertical direction is hindered by the cover part 322 or the bottom part 323 of the engagement receiving part 320, and movement of the engagement protrusion part 220 in a rotation direction hindered by the side wall 321 of the engagement receiving part 320. Therefore, movement of the engagement protrusion part 220 other than movement in the right-handed direction (clockwise direction) around the rotation axis O is restricted. In other words, the engagement protrusion part 220 is engaged with the engagement receiving part 320 to thereby be in the engaged state in which the movement of the engagement protrusion part 220 in the vertical direction is restricted by the engagement receiving part 320.

In the engaged state, the engagement protrusion part 220 does not have to always come in contact with at least one of the side wall 321, the cover part 322 and the bottom part 323 of the engagement receiving part 320 as long as movement of the engagement protrusion part 220 at least in the vertical direction is restricted as described above. However, it is preferable that the engagement protrusion part 220 in the engaged state always comes in contact with the side wall 321, the cover part 322 or the bottom part 323 of the engagement receiving part 320 to maintain a constant positional relationship with respect to the engagement receiving part 320. As described above, the fixing tool 100a becomes in the engaged state, such that the medical instrument 1 becomes in the fixed state. The description in this paragraph is similarly applied to a relationship between an engagement protrusion part and an engagement receiving part according to another embodiment to be described below.

Although the case in which the engagement protrusion part 220a, the engagement protrusion part 220b, the engagement protrusion part 220c and the engagement protrusion part 220d are sequentially engaged with the engagement receiving part 320a, the engagement receiving part 320b, the engagement receiving part 320c and the engagement receiving part 320d, respectively, is illustrated in FIG. 4B, the engagement protrusion part 220a may be engaged with any one of the engagement receiving parts 320a to 320d. That is, the positional relationship between the first and second engaging members 200a and 300a according to the present embodiment in the engaged state can take four forms.

In order to change the engaged state of the fixing tool 100a as illustrated in FIG. 4B to the unengaged state, after rotating the first engaging member 200*a* in the clockwise direction with respect to the second engaging member 300*a* to thereby be in the state illustrated in FIG. 4A, the first engaging member 200*a* may be pulled in the upward direction.

As described above, the first engaging member 200*a* can be engaged with the second engaging member 300*a* by rotation with respect to the second engaging member 300*a*, and the engagement can be released by rotation in a direction opposite to the engagement. Therefore, in the medical instrument 1 according to the present embodiment, the fixed state and the non-fixed state can be easily converted by the fixing tool 100*a*.

At the time of using the medical instrument 1, the attaching member 20 is attached to the skin of the subject through the attachment surface 22. Here, the medical instrument 1 may be set in the fixed state in advance and then be attached or become in the fixed state after the attaching member 20 is attached to the skin of the subject in the non-fixed state. The medical instrument 1 is set in the fixed state in advance and then attached to the skin of the subject, which is preferable in that the first and second engaging members 200*a* and 300*a* are easily aligned. This is also equally applied to other embodiments to be described below.

FIG. 5 is a cross-sectional view taken along line A-A of FIG. 4B in a state in which the subject uses the medical instrument 1 in the fixed state. Illustration of an internal structure of the medical device 10*a* is omitted. As illustrated in FIG. 5, after the medical instrument 1 becomes in the fixed state, it is possible to use the medical instrument 1 by partially protruding the needle-like member X from the opening part 231 provided in the first engaging member 200*a*, passing the needle-like member X through the passing hole 311 of the central convex part 310, and inserting the needle-like member X into the body from the skin surface SS of the subject. In other embodiments to be described below, configurations corresponding to the needle-like member X, the hollow part 13 receiving the needle-like member X and the passing hole 311 through which the needle-like member X passes are not described, but these configurations can be appropriately provided similarly in the present embodiment.

Figure 6:
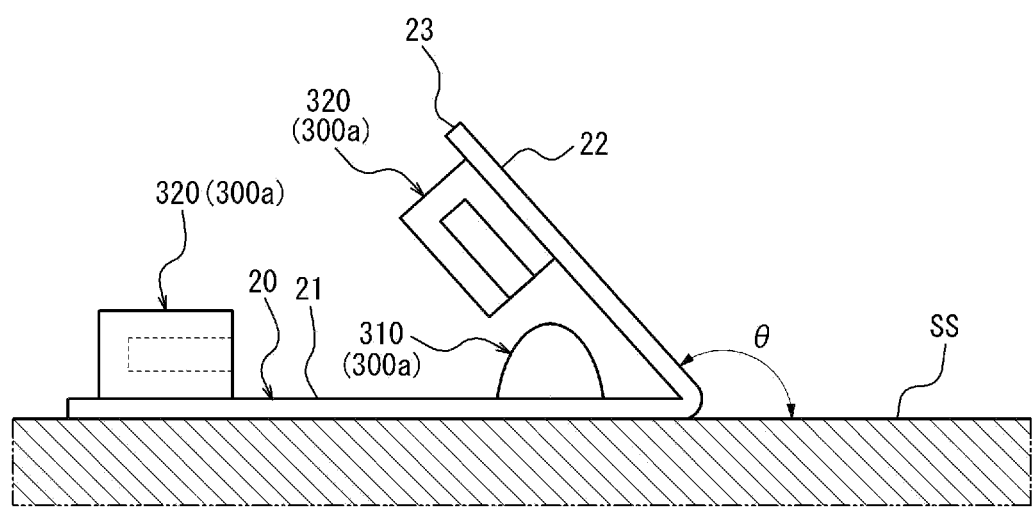
FIG. 6 is a view illustrating a process of detaching the medical instrument illustrated in FIG. 1 from the skin.

FIG. 6 is a schematic view illustrating a form in which the medical instrument 1 is detached from the skin surface SS. When uses of the medical instrument 1 is terminated, in the medical instrument 1, in the case in which the needle-like member X is inserted into the skin, after taking the needle-like member X out, engagement between the first and second engaging members 200*a* and 300*a* is released, such that the medical device 10*a* is detached from the attaching member 20 to thereby be in the non-fixed state. Thereafter, as illustrated in FIG. 6, the remaining attaching member 20 is detached from the skin.

When the attaching member 20 is detached from the skin, the attaching member 20 is detached from an arbitrary end portion along an outer periphery thereof, for example, a right end portion 23 illustrated in FIG. 6 in the horizontal direction. Here, the right end portion 23 is pulled so that an angle θ between the skin surface SS of the subject and the attachment surface 22 of the attaching member 20 is a predetermined angle (for example, an angle of 90 degrees or more). As described above, the right end portion 23 is pulled so that the angle θ is a predetermined angle, such that force applied to the skin at the time of detaching the attaching member 20 can be dispersed, thereby making it possible to alleviate peeling of the epidermis or pain felt by the subject.

When the attaching member 20 is detached from the skin, because the second engaging member 300*a* generally has higher rigidity than that of the attaching member 20, the angle θ may be smaller than the desired angle in a site in which the second engaging member 300*a* is provided. However, because an area of the second engaging member 300*a* occupying the fixing surface 21 of the attaching member 20 when viewed from the above is smaller than that of the medical device 10*a* and a height of the second engaging member 300*a* in the vertical direction is also low, it is easy to secure the angle θ to be large as compared to the case of detaching the attaching member from the skin surface SS together with the medical device. Therefore, it is possible to further decrease force applied to the skin at the time of detaching the attaching member 20, thereby making it possible to alleviate pain felt by the subject. Further, the central convex part 310 and the engagement receiving part 320 of the second engaging member 300*a* are provided on the attaching member 20 to be spaced apart from each other. For this reason, a distance between the central convex part 310 and the engagement receiving part 320 can be increased. Thereby, when the attaching member 20 is detached, because the timings at which the central convex part 310 and the engagement receiving part 320 are detached from the skin easily deviate from each other and at the same time, it is possible to decrease an area of a site in which the second engaging member 300*a* to be detached is provided, the force applied to the skin can be further dispersed, thereby making it possible to alleviate the pain felt by the subject.

Figure 7A:
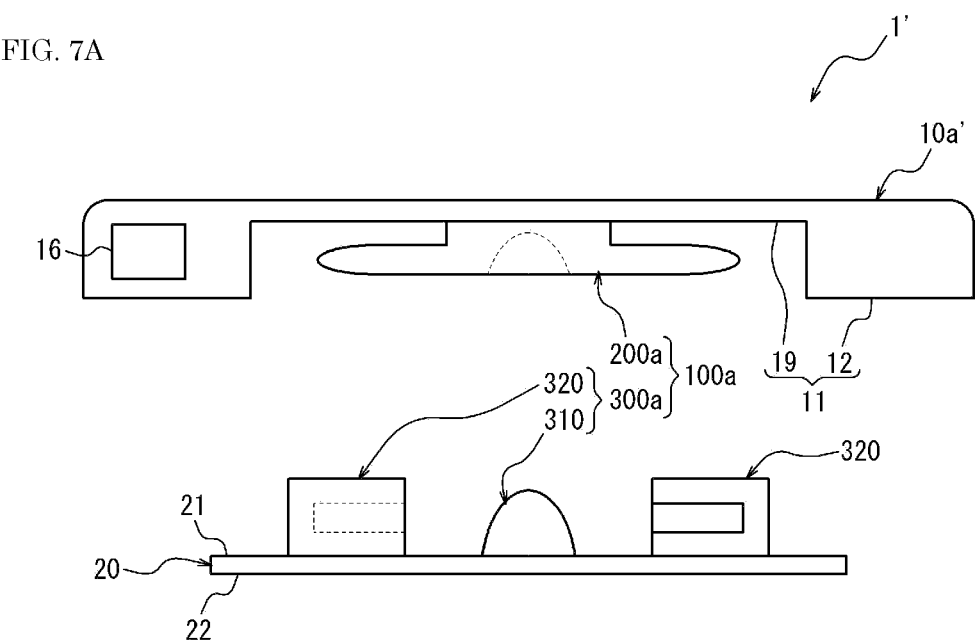
FIGS. 7A and 7B are front views illustrating a modified example of the medical instrument illustrated in FIG. 1.
Figure 7B:
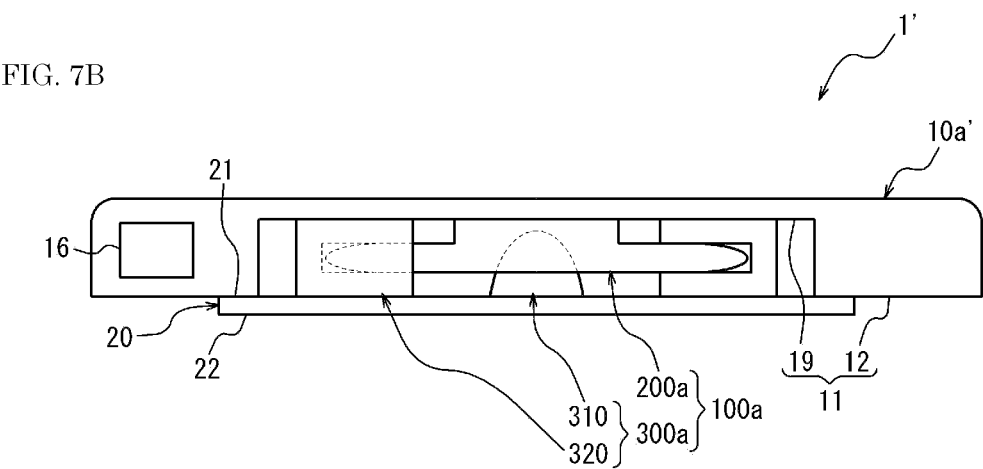

FIGS. 7A and 7B are front views illustrating a medical instrument 1' according to a modified example of the medical instrument 1, wherein FIG. 7A illustrates a non-fixed state, and FIG. 7B illustrates a fixed state. In the medical instrument 1', the medical device 10*a* of the medical instrument 1 is replaced with a medical device 10*a*'. In FIG. 7, illustration of a needle-like member X, a hollow part accommodating the needle-like member X and the like is omitted.

In the medical device 10*a*', a thickness of a portion directly above a bottom central part 19 in which a first engaging member 200*a* is provided in a vertical direction is decreased to be smaller than that of the medical device 10*a* by disposing a circuit system 16, such as an internal control unit, directly above a bottom peripheral part 12. Because other configurations of the medical device 10*a*' are the same as those of the medical device 10*a*, a description thereof is omitted.

A thickness of the medical instrument 1' in the vertical direction in the fixed state can be decreased as illustrated in FIG. 7A. As a result, because the medical instrument 1' is unlikely to serve as an obstacle at the time of use, burden on the subject at the time of use can be decreased. Meanwhile, because in the medical device 10*a*', the circuit system 16 is disposed directly above the bottom peripheral part 12, an area of a bottom surface 11 when viewed from the bottom surface 11 tends to be large. However, because burden on the subject at the time of detaching the medical instrument 1' from the skin surface SS is irrelevant to the area of the bottom surface 11 of the medical device 10*a*' when viewed from the bottom surface, it is possible to decrease the burden on the subject when the attaching member 20 is detached.

Figure 8B:
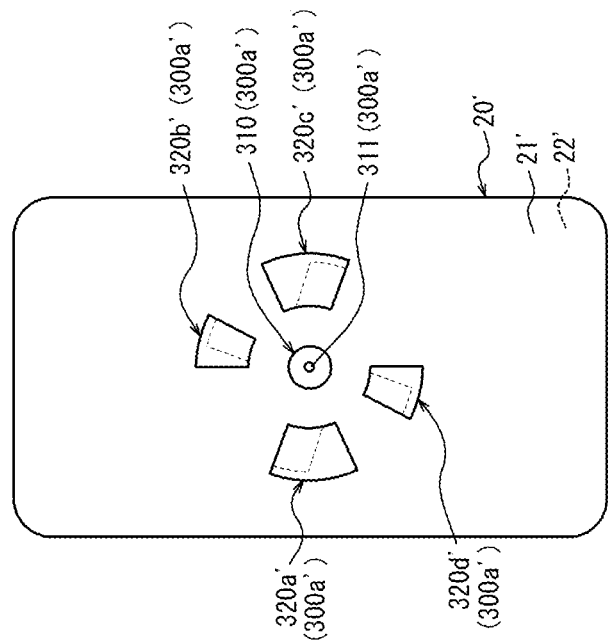
FIGS. 8A and 8B are views illustrating another modified example of the medical instrument illustrated in FIG. 1.
Figure 8A:
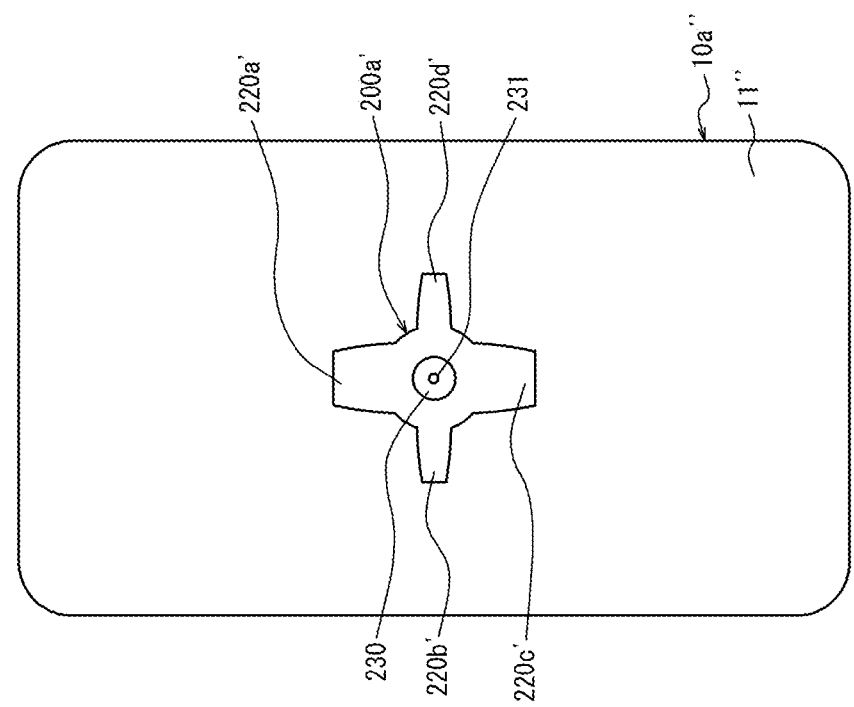

FIGS. 8A and 8B are views illustrating another modified example of the medical instrument 1, wherein FIG. 8A is a bottom view of a medical device 10*a*" according to the modified example in which a first engaging member 200*a*' is provided according to the modified example, and FIG. 8B is a top view of an attaching member 20' according to the modified example on which a second engaging member 300a' according to the modified example is provided.

As illustrated in FIG. 8A, the medical instrument 1 may include the first engaging member 200a' having engagement protrusion parts 220a' to 220d' of which shapes or sizes are different from each other instead of the first engaging member 200a. Further, as illustrated in FIG. 8B, the medical instrument 1 may include the second engaging member 300a' having engagement receiving parts 320a' to 320d' of which shapes or sizes are different from each other instead of the second engaging member 300a. The engagement protrusion parts 220a' and 220c' and the engagement receiving parts 320a' and 320c' constitute pairs engaging with each other, respectively, and do not engage with the engagement receiving parts 320b' and 320d'. Similarly, the engagement protrusion parts 220b' and 220d' and the engagement receiving parts 320b' and 320d' constitute pairs engaging with each other, respectively, and do not engage with the engagement receiving parts 320a' and 320c'.

Each of pairs of the engagement protrusion part and the engagement receiving part engaging with each other, among the engagement protrusion parts 220a' to 220d' and the engagement receiving parts 320a' to 320d', has a shape, size and position, at least one of which is different from that of the other pairs. As described above, the medical instrument according to the modified example includes a plurality of pairs of the engagement protrusion part and the engagement receiving part engaging with each other among the engagement protrusion parts 220a' to 220d' and the engagement receiving parts 320a' to 320d' (in the present example, four pairs), and each of the pairs of the engagement protrusion parts 220a' to 220d' and the engagement receiving parts 320a' to 320d' engaging with each other has a shape, size and position, at least one of which is different from that of the other pairs. Therefore, in the medical instrument 1, it is possible to restrict a positional relationship when the first and second engaging members 200a' and 300a' are in the fixed state, such that a fixed state in the desired positional relationship can be implemented always.

Further, the medical instrument 1 may include a medical device 10a" having a substantially rectangular bottom surface 11" instead of the medical device 10a; and an attaching member 20' having a substantially rectangular shape instead of the attaching member 20 as illustrated in FIGS. 8A and 8B.

Second Embodiment

Figure 9:
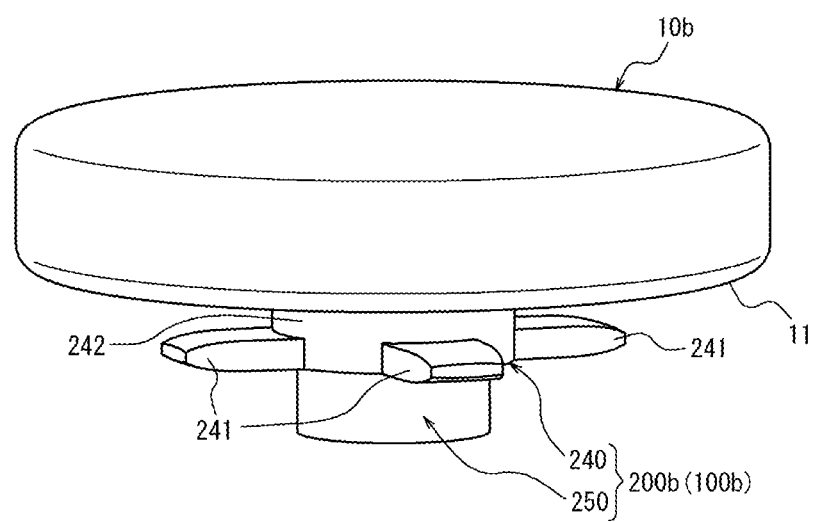
FIG. 9 is an external perspective view illustrating a part of a medical instrument according to a second embodiment of the present invention.
Figure 10A:
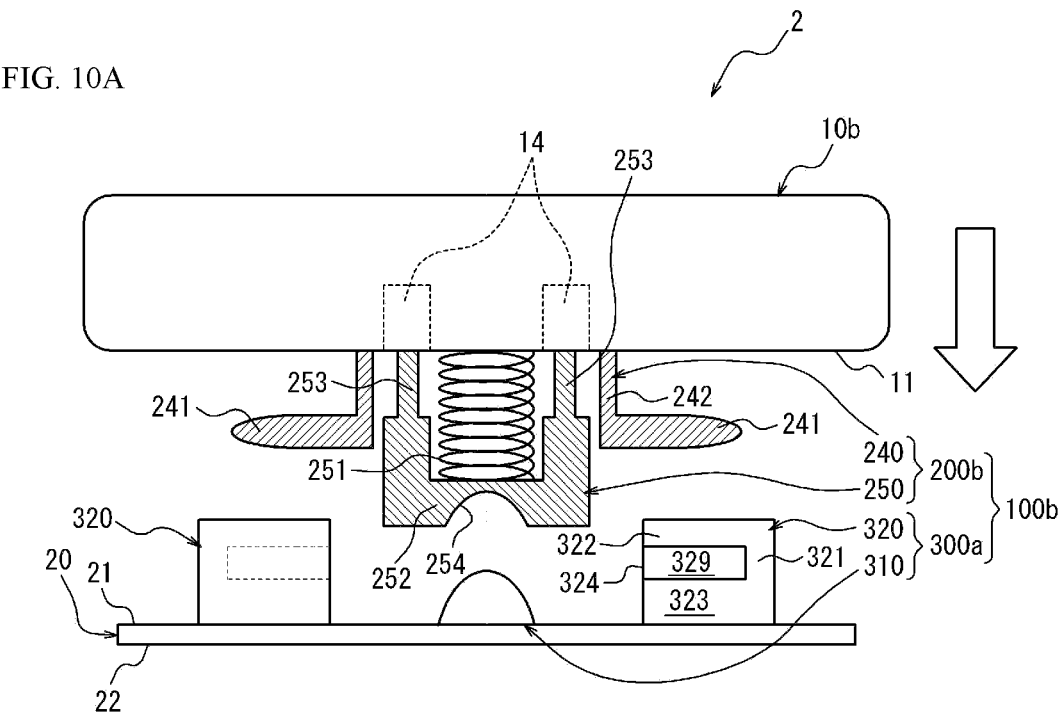
FIGS. 10A and 10B are views illustrating a process of engaging a fixing tool.
Figure 10B:
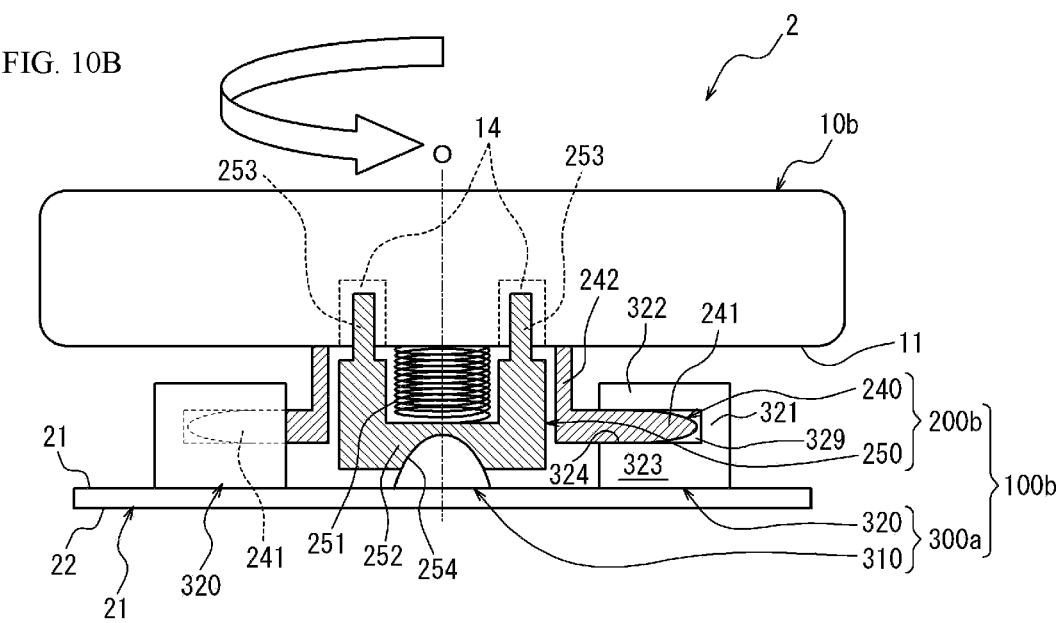

FIG. 9 is an external perspective view illustrating a medical device 10b and a first engaging member 200b of a medical instrument 2 according to a second embodiment of the present invention. Further, FIGS. 10A and 10B are views illustrating a process of engaging a fixing tool 100b of the medical instrument 2, wherein FIG. 10A illustrates a non-fixed state, and FIG. 10B illustrates a fixed state. A white arrow having a black edge in FIG. 10A indicates a direction in which the medical device 10b moves, and a white arrow having a black edge in FIG. 10B indicates a direction in which the medical device 10b rotates. In FIGS. 10A and 10B, for convenience of explanation, the first engaging member 200b except for an elastic part 251 is illustrated as a cross-sectional view.

As illustrated in FIGS. 9, 10A and 10B, the medical instrument 2 includes the medical device 10b; the attaching member 20; and a fixing tool 100b fixing the medical device 10b to the attaching member 20.

Because the medical device 10b is the same configuration as the medical device 10a according to the first embodiment except that an accommodation part 14 to be described below is formed therein, a description thereof is omitted.

The fixing tool 100b has the first engaging member 200b provided on the medical device 10b; and a second engaging member 300a provided on an fixing surface 21 of the attaching member 20. The fixing tool 100b is a member for allowing the medical instrument 2 in the non-fixed state to be in the fixed state by connecting the medical device 10b and the attaching member 20 to each other.

The first engaging member 200b has a tubular protrusion part 240; and an energizing part 250. As illustrated in FIG. 10A, the tubular protrusion part 240 includes: a cylindrical tube part 242 provided on a bottom surface 11 of the medical device 10b and extending downwardly from the bottom surface 11 of the medical device 10b; and an engagement protrusion part 241 extending from a lower end of the tube part 242 in a parallel direction. In the present embodiment, the first engaging member 200b has four engagement protrusion parts 241 protruding outwardly from the lower end of the tubular protrusion part 240 in a diameter direction and disposed at substantially equal intervals in a circumferential direction, and the four engagement protrusion parts 241 have substantially the same shape and size as each other.

The energizing part 250 is provided on the bottom surface 11 of the medical device 10b in the tube part 242 separately from the tubular protrusion part 240 and has the elastic part 251, a bottom part 252, and an accommodated part 253. The accommodated part 253 is accommodated in a hollow accommodation part 14 formed in the bottom surface 11 of the medical device 10b to thereby be movable in a vertical direction. The bottom part 252 is connected to the accommodated part 253, and a central concave part 254 recessed in an upward direction is formed therein. The elastic part 251 is, for example, an elastic member having a coil spring shape, and is a member contracted when pressed in the vertical direction and energizing a pressing object in the vertical direction by a restoring force. The elastic part 251 is disposed between the bottom surface 11 of the medical device 10b and the bottom part 252.

As illustrated in FIG. 10A, the first engaging member 200b is installed from above the second engaging member 300a. Here, a positional relationship between the engagement protrusion part 241 and the engagement receiving part 320 is a positional relationship in which each of the engagement protrusion parts 241 is disposed between the engagement receiving parts 320 as illustrated in FIG. 4A.

When the first engaging member 200b is pushed from above the second engaging member 300a, as illustrated in FIG. 10B, the central concave part 254 comes in contact with a central convex part 310, such that the first engaging member 200b is supported by the central convex part 310. Here, the bottom part 252 is pushed upwardly by the central convex part 310, such that the elastic part 251 is contracted, and at the same time, the accommodated part 253 moves upward to thereby be accommodated in the accommodation part 14. In this case, the central convex part 310 and the central concave part 254 serve as a support part and a supported part, respectively, and constitute a rotation axis O in the vertical direction. The first and second engaging members 200b and 300a can rotate around the rotation axis O with respect to each other. Further, the engagement protrusion part 241 is disposed to extend in the diameter direction around the rotation axis O. More specifically, the engagement protrusion part 241 according to the present embodiment is disposed to protrude outwardly from the rotation axis O in the diameter direction.

In the case of rotating the first engaging member 200*b* with respect to the second engaging member 300*a* in a counterclockwise direction in a state in which the first engaging member 200*b* is pushed from above, the engagement protrusion part 241 passes through an opening part 324 of the engagement receiving part 320 to thereby be accommodated in a hollow part 329 as illustrated in FIG. 10B. Therefore, similarly to the engagement protrusion part 220 according to the first embodiment, the engagement protrusion part 241 is engaged with the engagement receiving part 320 to thereby be in an engaged state in which movement of the engagement protrusion part 241 in the vertical direction is restricted by the engagement receiving part 320.

When the pushing of the first engaging member 200*b* from above is terminated in the engaged state, the elastic part 251 energizes the bottom part 252 in a downward direction and energizes the medical device 10*b* in an upward direction by a restoring force. As a result, because the energizing part 250 energizes the tubular protrusion part 240 including the engagement protrusion part 241, directly provided on the medical device 10*b* in an upward direction opposite to a downward direction corresponding to a direction in which the attaching member 20 is positioned, the engagement protrusion part 241 can come in contact with a cover part 322 of the engagement receiving part 320. Therefore, the medical instrument 2 includes the energizing part 250, thereby making it possible to more firmly maintain the engaged state of the engagement protrusion part 241 and the engagement receiving part 320.

In order to change the engaged state of the fixing tool 100*b* as illustrated in FIG. 10B to an unengaged state, the first engaging member 200*b* may be pulled in the upward direction after rotating the first engaging member 200*b* in a clockwise direction with respect to the second engaging member 300*a* while pushing the first engaging member 200*b* in the downward direction. Therefore, similarly to the medical instrument 1 according to the first embodiment, in the medical instrument 2 according to the present embodiment, the fixed state and the non-fixed state can be easily converted by the fixing tool 100*b*.

Figure 11:
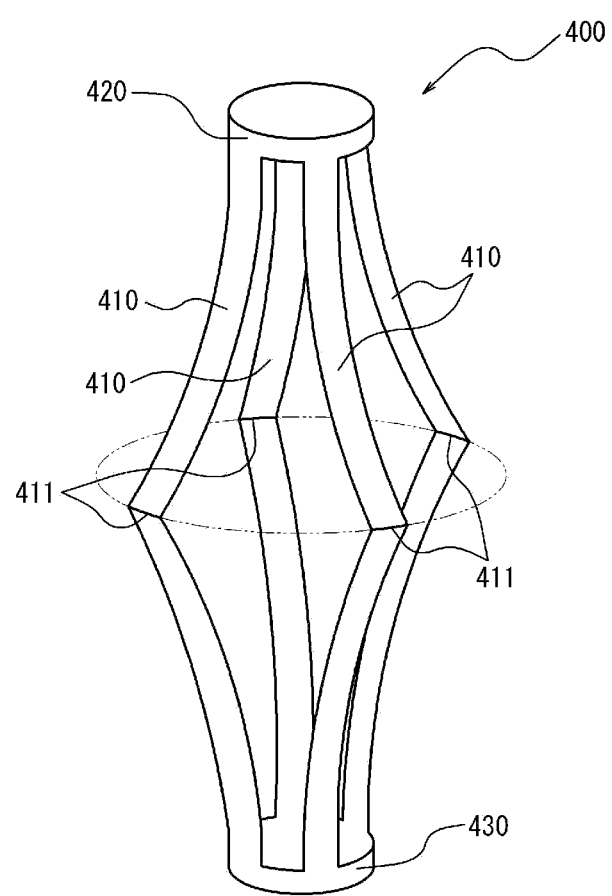
FIG. 11 is an external perspective view illustrating a diameter variable body.

A diameter variable body 400 that is the same structure as diameter variable parts 263 and 273 used in third and fourth embodiments to be described below is described with reference to FIG. 11. The diameter variable body 400 has a substantially circular plate-shaped upper part 420; a substantially circular plate-shaped lower part 430; and a strip-shaped connection part 410 connecting outer edges of the upper and lower parts 420 and 430 to each other and having a length in a vertical direction. A plurality of connection parts 410 (four connection parts in the present embodiment) are disposed at substantially equal intervals at the outer edges of the upper and lower parts 420 and 430, and a folding part 411 is formed in the vicinity of the center thereof in the vertical direction. When the diameter variable body 400 moves so as to be contracted in the vertical direction, that is, so as to allow the upper and lower parts 420 and 430 to approach each other in the vertical direction, the plurality of connection parts 410 is expanded in a direction (horizontal direction) perpendicular to the vertical direction (a diameter is increased). Meanwhile, the diameter variable body 400 is elongated in the vertical direction. That is, when the upper and lower parts 420 and 430 move so as to be apart from each other in the vertical direction, the plurality of connection parts 410 become narrow in the horizontal direction (the diameter is decreased).

Third Embodiment

Figure 12A:
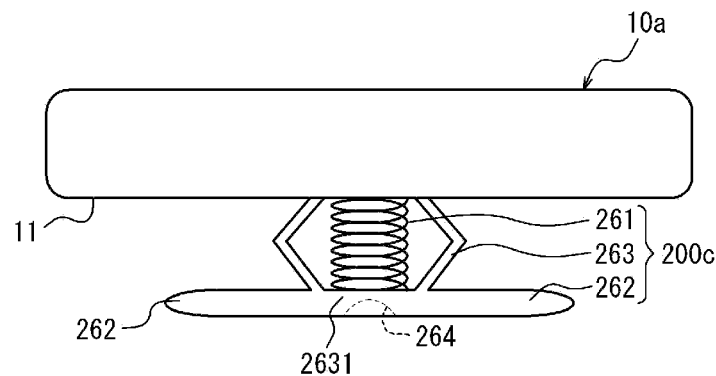
FIGS. 12A-12C are views illustrating a process of engaging a fixing tool of a medical instrument according to a third embodiment of the present invention.
Figure 12B:
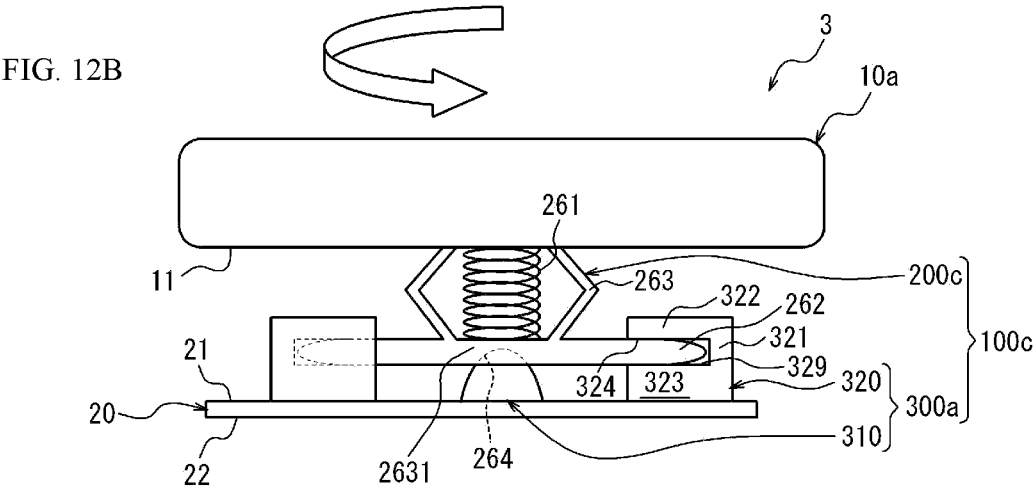
Figure 12C:
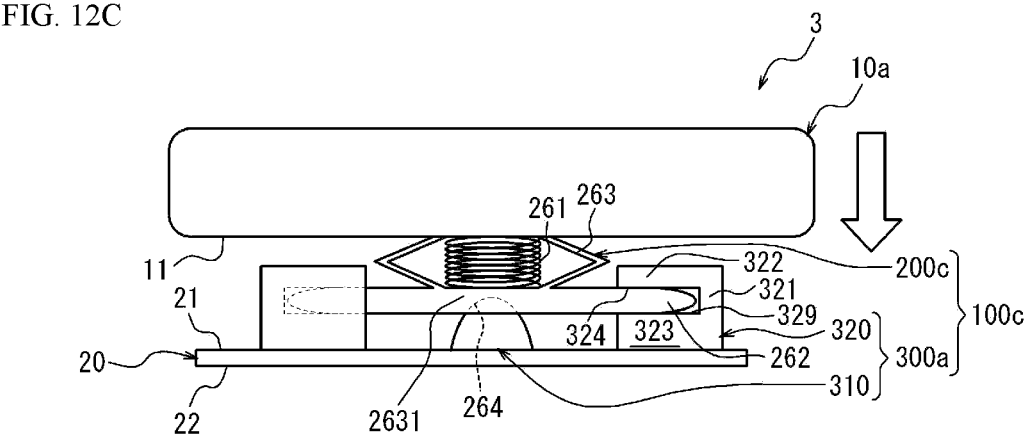

FIGS. 12A-12C are views illustrating a process of engaging a fixing tool 100*c* of a medical instrument 3 according to a third embodiment of the present invention, wherein FIG. 12A illustrates a non-fixed state, and FIGS. 12B and 12C illustrate a fixed state. FIG. 12C illustrates a state in which a medical device 10*a* is further pushed from the state illustrated in FIG. 12B. A white arrow having a black edge in FIG. 12B indicates a direction in which the medical device 10*a* rotates, and a white arrow having a black edge in FIG. 12C indicates a direction in which the medical device 10*a* is pushed.

As illustrated in FIGS. 12B and 12C, the medical instrument 3 includes the medical device 10*a*; an attaching member 20; and the fixing tool 100*c* fixing the medical device 10*a* to the attaching member 20.

The fixing tool 100*c* has a first engaging member 200*c* provided in the medical device 10*a*; and a second engaging member 300*a* provided on an fixing surface 21 of the attaching member 20. The fixing tool 100*c* is a member for allowing the medical instrument 3 in the non-fixed state to be in the fixed state by connecting the medical device 10*a* and the attaching member 20 to each other.

The first engaging member 200*c* includes an elastic part 261; an engagement protrusion part 262; and the diameter variable part 263. The diameter variable part 263 is provided on a bottom surface 11 of the medical device 10*a* and extending downwardly from the bottom surface 11 to have a bottom part 2631. The engagement protrusion part 262 extends from the bottom part 2631 of a lower end of the diameter variable part 263 in a parallel direction. A central concave part 264 recessed in an upward direction is formed in a bottom surface of the bottom part 2631 of the lower end of the diameter variable part 263. The first engaging member 200*c* has four engagement protrusion parts 262 extending in a diameter direction, similarly to the engagement protrusion part 220 according to the first embodiment, and the four engagement protrusion parts 262 have substantially the same shape and size as each other. The elastic part 261 is the same elastic member as the elastic part 251 according to the second embodiment, is contracted when pressed in the vertical direction, and energizes a pressing object in the vertical direction by a restoring force. The elastic part 261 is disposed between the bottom surface 11 of the medical device 10*a* and the bottom part 2631. The diameter variable part 263 and the elastic part 261 constitute an energizing part together.

First, the first engaging member 200*c* illustrated in FIG. 12A is placed above the second engaging member 300*a*. Here, a positional relationship between the engagement protrusion part 262 and an engagement receiving part 320 is a positional relationship in which each of the engagement protrusion parts 262 is disposed between the engagement receiving parts 320 as illustrated in FIG. 4A.

In the case of rotating the first engaging member 200*c* with respect to the second engaging member 300*a* in a counterclockwise direction in a state in which the first engaging member 200*c* is placed above the second engaging member 300*a*, the engagement protrusion part 262 passes through an opening part 324 of the engagement receiving part 320 to thereby be accommodated in a hollow part 329 as illustrated in FIG. 12B. Therefore, similarly to the engagement protrusion part 220 according to the first embodiment, the engagement protrusion part 262 is engaged with the engagement receiving part 320 to thereby be in an engaged state in which movement of the engagement protrusion part 262 in the vertical direction is restricted by the engagement receiving part 320.

In the engaged state illustrated in FIG. 12 B, when the first engaging member 200c is further pushed from above, as illustrated in FIG. 12C, the elastic part 261 is contracted and energizes the bottom part 2631 of the diameter variable part 263 in a downward direction, and energizes the medical device 10a in an upward direction by a restoring force. As a result, because the elastic part 261 energizes the engagement protrusion part 262 connected to the bottom part 2631 in a direction in which the attaching member 20 is positioned, the engagement protrusion part 262 comes in contact with a bottom part 323 of the engagement receiving part 320. Therefore, the medical instrument 2 includes the energizing part (the diameter variable part 263 and the elastic part 261), thereby making it possible to more firmly maintain the engaged state of the engagement protrusion part 262 and the engagement receiving part 320.

In order to continuously push the first engaging member 200c from above in the engaged state, a locking mechanism maintaining the first engaging member 200c in a state in which the elastic part 261 is compressed is provided in the medical device 10a. The locking mechanism as described above can be realized by various configurations; for example, it can be a locking mechanism that maintains a constant distance between the medical device 10a and the second engaging member 300a.

In order to change the engaged state of the fixing tool 100c as illustrated in FIG. 12C to an unengaged state, after releasing the pushing of the first engaging member 200c from above, the first engaging member 200c is rotated with respect to the second engaging member 300a in a clockwise direction, and the first engaging member 200c is pulled upward. Therefore, similarly to the medical instrument 1 according to the first embodiment, in the medical instrument 3 according to the present embodiment, the fixed state and the non-fixed state can be easily converted by the fixing tool 100c.

Fourth Embodiment

Figure 13A:
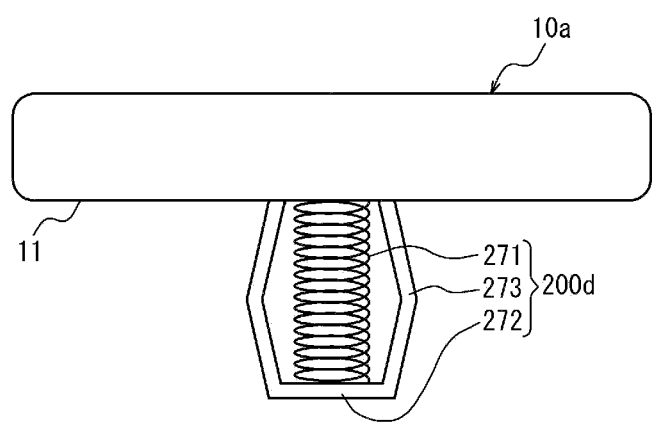
FIGS. 13A and 13B are views illustrating a part of a medical instrument according to a fourth embodiment of the present invention.
Figure 13B:
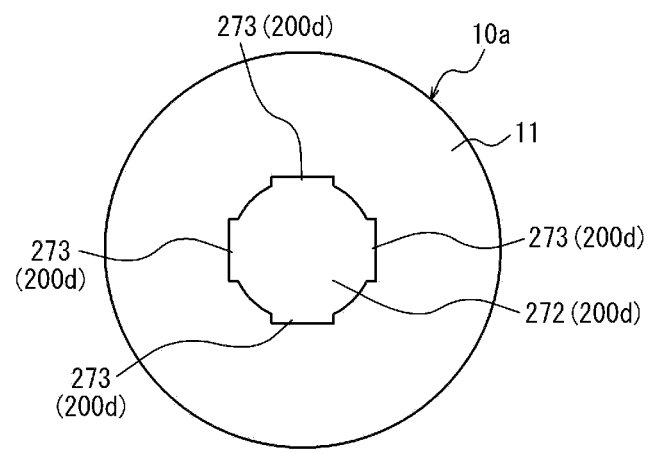
Figure 14A:
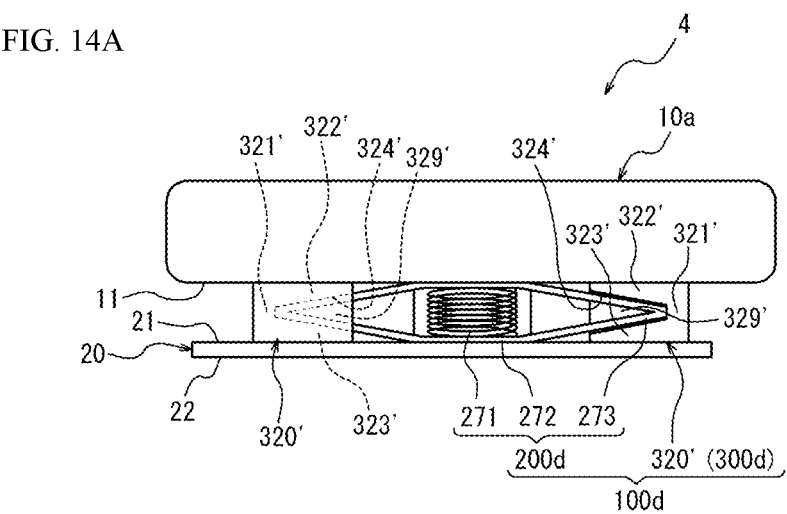
FIGS. 14A and 14B are views illustrating a form in which a fixing tool of the medical instrument illustrated in FIG. 13 is engaged.
Figure 14B:
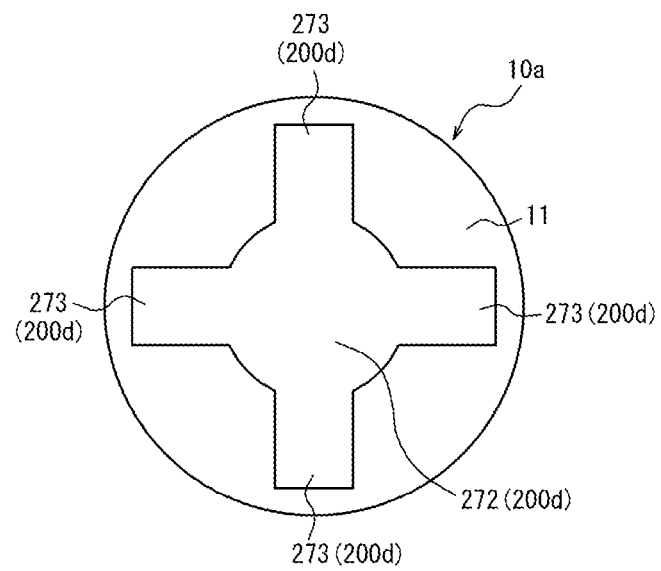

FIGS. 13A and 13B are views illustrating a medical device 10a and a first engaging member 200d of a medical instrument 4 according to a fourth embodiment of the present invention in a non-fixed state, wherein FIG. 13A is a front view and FIG. 13B is a bottom view. Further, FIGS. 14A and 14B are views illustrating a fixing tool 100d of the medical instrument 4 in a fixed state, wherein FIG. 14A is a front view of the medical instrument 4, and FIG. 14B is a bottom view of the medical device 10a and the first engaging member 200d.

The medical instrument 4 includes the medical device 10a; an attaching member 20; and the fixing tool 100d fixing the medical device 10a to the attaching member 20.

The fixing tool 100d has a first engaging member 200d provided in the medical device 10a; and a second engaging member 300d provided on an fixing surface 21 of the attaching member 20. The fixing tool 100d is a member for allowing the medical instrument 4 in the non-fixed state to be in the fixed state by connecting the medical device 10a and the attaching member 20 to each other.

The first engaging member 200d includes an elastic part 271; a bottom part 272; and a diameter variable part 273. The diameter variable part 273 is provided on a bottom surface 11 of the medical device 10a and extends downwardly from the bottom surface 11 to thereby be connected to the bottom part 272. A diameter of the diameter variable part 273 can be expanded in a parallel direction similarly to the diameter variable body 400 illustrated in FIG. 11. In the present embodiment, the diameter variable part 273 has four strip-shaped connection parts 410 (see FIG. 11), and the four strip-shaped connection parts 410 have substantially the same shape and size as each other. In a state in which external force is not applied, the diameter of the diameter variable part 273 is decreased as illustrated in FIG. 13B, but in the case in which the diameter variable part 273 is pressed in a vertical direction, the diameter is expanded as illustrated in FIGS. 14A and 14B, such that the diameter variable part 273 constitutes an engagement protrusion part. The elastic part 271 is the same elastic member as the elastic part 251 according to the second embodiment, is contracted when pressed in the vertical direction, and energizes a pressing object in the vertical direction by a restoring force. The elastic part 271 is disposed between the bottom surface 11 of the medical device 10a and the bottom part 272.

The second engaging member 300d is a member engageable with the first engaging member 200d by rotation with respect to the first engaging member 200d and has an engagement receiving part 320'. A hollow part 329' is formed in the engagement receiving part 320' and is in communication with the outside through an opening part 324' formed in a portion of a side surface of the engagement receiving part 320' in the parallel direction. More specifically, the engagement receiving part 320' has a cover part 322' covering an upper portion thereof; a side wall 321' positioned in the periphery in the parallel direction and having the opening part 324 formed therein; and a bottom part 323' covering a lower portion thereof. As illustrated in FIG. 14A, in order to allow the cover part 322' and the bottom part 323' to correspond to a shape of the diameter variable part 273 of which the diameter is expanded, in the second engaging member 300d, the hollow part 329' is inclined so that the hollow part 329' becomes narrow in the vertical direction as a distance from the center of the fixing tool 100d is increased. Because other configurations other than the above-mentioned configuration of the engagement receiving part 320' are the same as those of the engagement receiving part 320 according to the first embodiment, a description thereof is omitted.

First, the first engaging member 200d illustrated in FIG. 13A is placed above the second engaging member 300d. Here, a positional relationship between the diameter variable part 273 and the engagement receiving part 320 is a positional relationship in which when the diameter is expanded, each of the diameter variable parts 273 is disposed between the engagement receiving parts 320 as illustrated in FIG. 4A.

When the first engaging member 200d is pushed toward the second engaging member 300d, the diameter of the diameter variable part 273 is expanded as illustrated in FIG. 14B, thereby forming the engagement protrusion part. In the case of rotating the first engaging member 200d with respect to the second engaging member 300d in a counterclockwise direction while pushing the first engaging member 200d in a downward direction, the diameter variable part 273 passes through the opening part 324' of the engagement receiving part 320' to thereby be accommodated in the hollow part 329' as illustrated in FIG. 14A. Therefore, similarly to the engagement protrusion part 220 according to the first embodiment, the diameter variable part 273 is engaged with the engagement receiving part 320' to thereby be in an engaged state in which movement of the diameter variable part 273 in the vertical direction is restricted by the engagement receiving part 320'.

When the pushing of the first engaging member 200d from above is terminated in the engaged state, the elastic part 271 energizes the bottom part 272 in the downward direction and energizes the medical device 10a in an upward direction by a restoring force. As a result, the diameter variable part 273 tends to be elongated in the vertical direction. Here, because an upper portion of the diameter variable part 273 comes in contact with the cover part 322' of the engagement receiving part 320' and a lower portion of the diameter variable part 273 comes in contact with the bottom part 323' of the engagement receiving part 320', elongation in the vertical direction is hindered. Therefore, the medical instrument 4 includes the elastic part 271 as the energizing part, thereby making it possible to more firmly maintain the engaged state of the diameter variable part 273 and the engagement receiving part 320.

In order to change the engaged state of the fixing tool 100d as illustrated in FIG. 14A to an unengaged state, the first engaging member 200d may be pulled in the upward direction after rotating the first engaging member 200d in a clockwise direction with respect to the second engaging member 300d while pushing the first engaging member 200d in the downward direction. Therefore, similarly to the medical instrument 1 according to the first embodiment, in the medical instrument 4 according to the present embodiment, the fixed state and the non-fixed state can be easily converted by the fixing tool 100d.

Fifth Embodiment

Figure 15A:
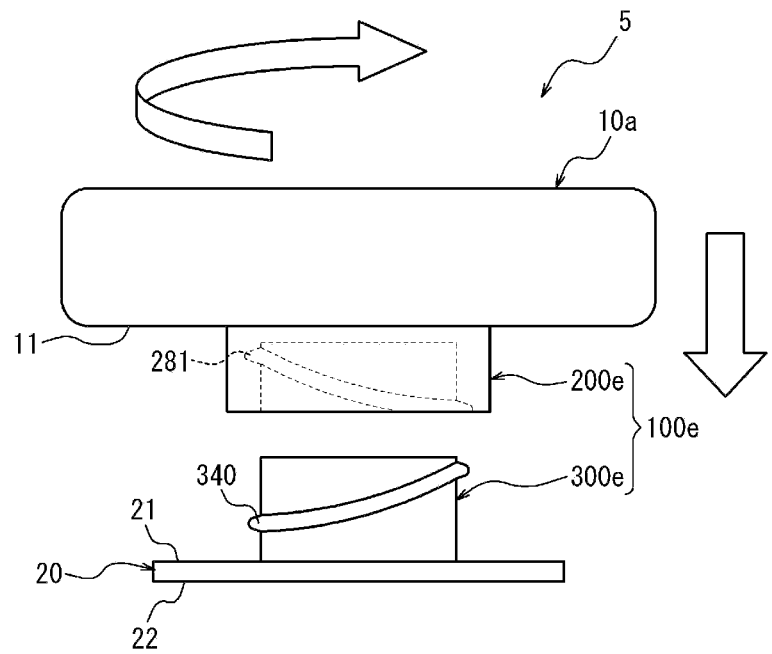
FIGS. 15A and 15B are front views of a medical instrument according to a fifth embodiment of the present invention.
Figure 15B:
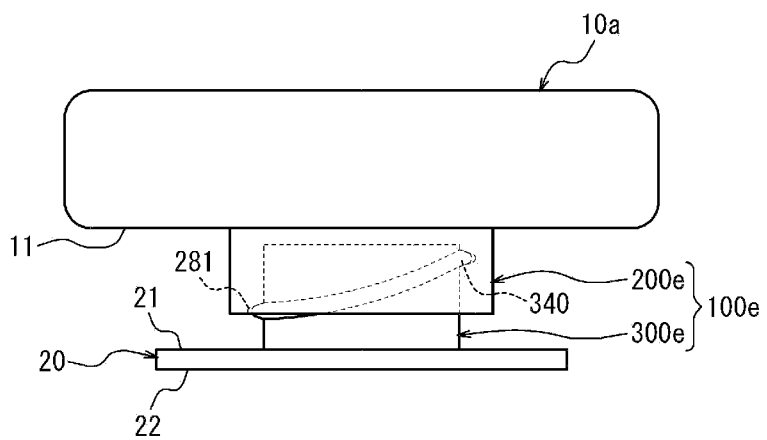

FIGS. 15A and 15B are front views of a medical instrument 5 according to a fifth embodiment, wherein FIG. 15A illustrates a non-fixed state and FIG. 15B illustrates a fixed state. White arrows having a black edge in FIG. 15A indicate a direction in which a medical device 10a rotates and a direction in which the medical device 10a is pushed when the non-fixed state is converted to the fixed state.

The medical instrument 5 includes the medical device 10a; an attaching member 20; and a fixing tool 100e fixing the medical device 10a to the attaching member 20.

The fixing tool 100e has a first engaging member 200e provided in the medical device 10a; and a second engaging member 300e provided on an fixing surface 21 of the attaching member 20. The fixing tool 100e is a member for allowing the medical instrument 5 in the non-fixed state to be in the fixed state by connecting the medical device 10a and the attaching member 20 to each other.

The first engaging member 200e is a cylindrical member provided on a bottom surface 11 of the medical device 10a, extending from the bottom surface 11 of the medical device 10a in a downward direction, and including a female screw part 281 on an inner peripheral surface.

The second engaging member 300e is a column-shape or cylindrical member engageable with the first engaging member 200e by rotation with respect to the first engaging member 200e and includes a male screw part 340 screwable with the female screw part 281 of the first engaging member 200e on an outer peripheral surface.

As illustrated in FIG. 15A, in the case of rotating the first engaging member 200e in a clockwise direction with respect to the second engaging member 300e while pushing the first engaging member 200e in a downward direction, the female screw part 281 of the first engaging member 200e is screwed to the male screw part 340 of the second engaging member 300e to thereby be in the engaged state as shown in FIG. 15B. In order to change the engaged state of the fixing tool 100e illustrated in FIG. 15B to an unengaged state, the first engaging member 200e may be rotated in a counterclockwise direction with respect to the second engaging member 300e.

Figure 16A:
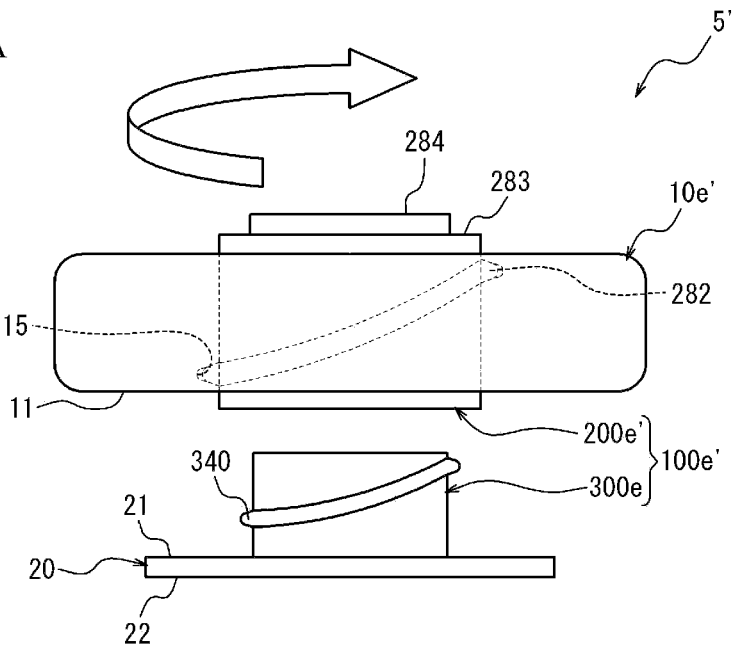
FIGS. 16A and 16B are views illustrating a modified example of the medical instrument illustrated in FIG. 15.
Figure 16B:
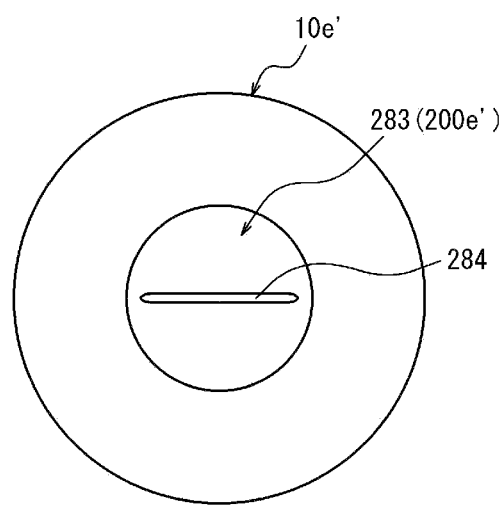

FIGS. 16A and 16B are views illustrating a medical instrument 5' according to a modified example of the medical instrument 5, wherein FIG. 16A is a front view illustrating a non-fixed state, and FIG. 16B is a top view. A white arrow having a black edge in FIG. 16A indicates a direction in which a medical device 10e' rotates when a non-fixed state is converted to a fixed state.

The medical instrument 5' includes the medical device 10e'; an attaching member 20; and a fixing tool 100e' fixing the medical device 10e' to the attaching member 20.

The medical device 10e has a cylindrical shape including a female screw part 15 on an inner peripheral surface. Because other configurations of the medical device 10e' are the same as those of the medical device 10a according to the first embodiment, a description thereof is omitted.

The fixing tool 100e' has a first engaging member 200e' provided in the medical device 10e'; and a second engaging member 300e provided on an fixing surface 21 of the attaching member 20. The fixing tool 100e' is a member for allowing the medical instrument 5' in the non-fixed state to be in the fixed state by connecting the medical device 10e' and the attaching member 20 to each other.

The first engaging member 200e' includes a male screw part 282 screwable with the female screw part 15 of the medical device 10e' on an outer peripheral surface thereof as well as a configuration of the first engaging member 200e. Further, the first engaging member 200e' includes a knob part 284 on a top surface 283. The first engaging member 200e' is configured so that the male screw part 282 can be screwed to the female screw part 15 from a lower side of the medical device 10e' to an upper side thereof.

As illustrated in FIG. 16A, in the case of rotating the knob part 284 of the first engaging member 200e' in a clockwise direction in a state in which the male screw part 282 of the first engaging member 200e' is screwed to the female screw part 15 of the medical device 10e', while the male screw part 282 of the first engaging member 200e' slides on the female screw part 15 of the medical device 10e', the first engaging member 200e' protrudes in a downward direction.

In the case of continuously rotating the knob part 284 in the clockwise direction in a state in which the first engaging member 200e' is placed on the second engaging member 300e, a female screw part 281 of the first engaging member 200e' is screwed to a male screw part 340 of the second engaging member 300e to thereby be in an engaged state as in the example illustrated in FIG. 15B. In order to change the engaged state of the fixing tool 100e' to an unengaged state, the knob part 284 of the first engagement 200e' may be rotated in a counterclockwise direction.

Sixth Embodiment

Figure 17A:
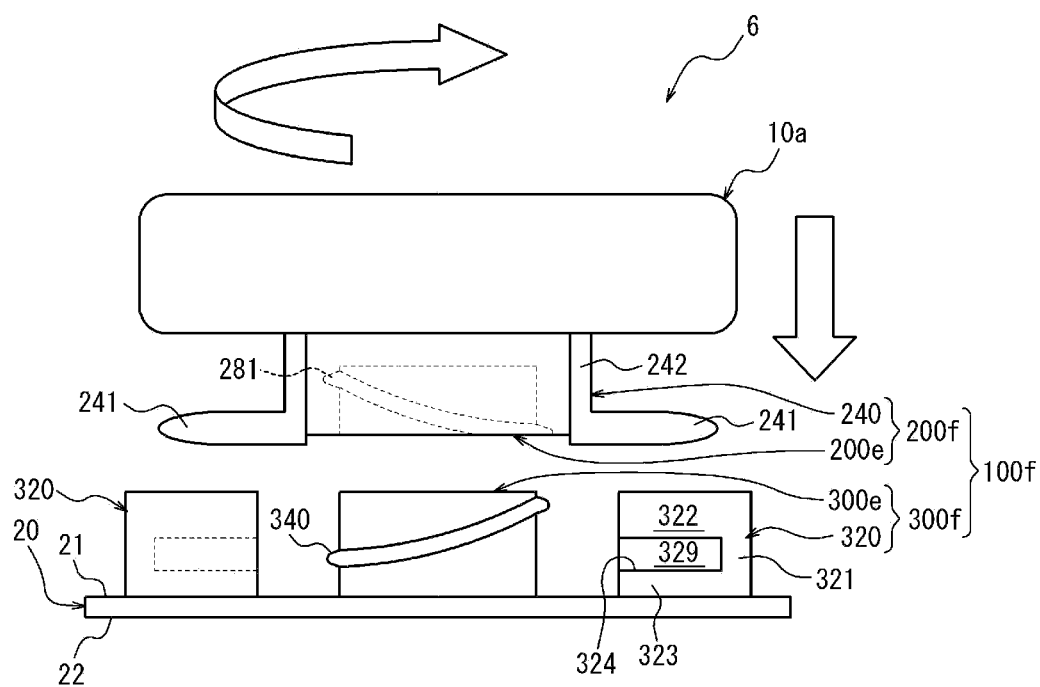
FIGS. 17A and 17B are front views of a medical instrument according to a sixth embodiment of the present invention.
Figure 17B:
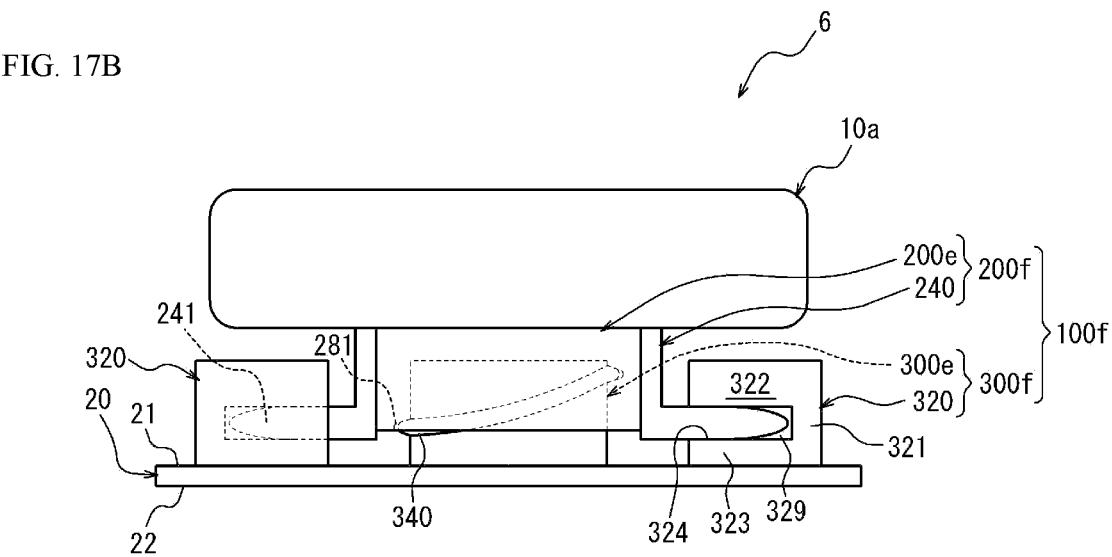

FIGS. 17A and 17B are front views of a medical instrument 6 according to a sixth embodiment, wherein FIG. 17A illustrates a non-fixed state and FIG. 17B illustrates a fixed state. White arrows having a black edge in FIG. 17A indicate a direction in which a medical device 10a rotates and a direction in which the medical device 10a is pushed when the non-fixed state is converted to the fixed state.

The medical instrument 6 includes the medical device 10a; an attaching member 20; and a fixing tool 100f fixing the medical device 10a to the attaching member 20.

The fixing tool 100f has a first engaging member 200f provided in the medical device 10a; and a second engaging member 300f provided on an fixing surface 21 of the attaching member 20. The fixing tool 100f is a member for allowing the medical instrument 6 in the non-fixed state to be in the fixed state by connecting the medical device 10a and the attaching member 20 to each other.

The first engaging member 200f has a tubular protrusion part 240; and a female screw body 200e. The tubular protrusion part 240 is the same configuration as the tubular protrusion part 240 in the first engaging member 200b according to the second embodiment. The female screw body 200e is the same configuration as the first engaging member 200e according to the fifth embodiment, and is disposed in an internal space of the tubular protrusion part 240.

The second engaging member 300f has a male screw body 300e; and an engagement receiving part 320. The male screw body 300e is the same configuration as the second engaging member 300e according to the fifth embodiment. The engagement receiving part 320 is the same configuration as the engagement receiving part 320 according to the first embodiment, and a positional relationship from the male screw body 300e is the same as the positional relationship from the central convex part 310 according to the first embodiment.

As illustrated in FIG. 17A, in the case of rotating the first engaging member 200f in a clockwise direction with respect to the second engaging member 300f while pushing the first engaging member 200f in a downward direction, a female screw part 281 of the female screw body 200e is screwed to a male screw part 340 of the male screw body 300e to thereby be in the engaged state as shown in FIG. 17B. Here, an engagement protrusion part 241 also passes through an opening part 324 of the engagement receiving part 320 to thereby be accommodated in a hollow part 329 and engaged with the engagement receiving part 320, thereby being in the engaged state. In this way, in addition to engagement between the female screw part 218 and the male screw part 340, engagement between the engagement protrusion part 241 and the engagement receiving part 320 can be obtained, so that the fixed state can be further stabilized.

In order to change the engaged state of the fixing tool 100f illustrated in FIG. 17B to an unengaged state, the first engaging member 200f may be rotated in a counterclockwise direction with respect to the second engaging member 300f.

The fixing tool according to each embodiment may be independent of the medical instrument. That is, the fixing tool may be a configuration including a first engaging member installable on a medical device; a second engaging member capable of being installed on an fixing surface of an attaching member; and an energizing member.

The medical device and the fixing tool according to the present invention are not limited to the configurations of the embodiments described above, and can be realized by various configurations without departing from the contents described in the claims. For example, although cases in which the bottom surface of the medical device or the attaching member according to each embodiment has a substantially circular or substantially rectangular shape are described, the bottom surface of the medical device or the attaching member may have any other arbitrary shape. For example, the bottom surface of the medical device or the attaching member may have a polygonal shape with three or five or more sides. Alternatively, the bottom surface of the medical device or the attaching member may have a circular shape or oval shape. Further, the bottom surface of the medical device and the attaching member may have different shapes from each other.

In addition, although in each of the embodiments, it is described that the first engaging member can be engaged with the second engaging member by rotating the first engaging member in a predetermined direction with respect to the second engaging member, a rotation direction is not particularly limited thereto, but may be a direction opposite thereto.

Further, although it is described that in the medical instrument 1 according to the first embodiment, the bottom peripheral part 12 of the bottom surface 11 protrudes downward more than the bottom central part 19, the bottom peripheral part 12 and the bottom central part 19 may be flat. However, it is preferable to provide the bottom peripheral part 12 so that the fixing tool is not exposed to the outside.

REFERENCE NUMERAL LIST 1, 1', 2, 3, 4, 5, 5', 6: medical instrument
10a, 10a', 10a", 10b, 10e': medical device
11, 11', 11": bottom surface
12, 12': bottom peripheral part
13, 13': hollow part
14: accommodation part
15: female screw part
16: circuit system
19: bottom central part
20, 20': attaching member
21, 21': fixing surface
22, 22': attachment surface
23: right end portion
100a to 100f, 100a', 100e': fixing tool
200a to 200d, 200a', 200e', 200f: first engaging member
200e: female screw body (first engaging member)
210: arm part
211: passing hole
220, 220a to 220d, 220a' to 220d': engagement protrusion part
230: central concave part (supported part)
231: opening part
240: tubular protrusion part
241: engagement protrusion part
242: tube part
250: energizing part (supported part)
251: elastic part
252: bottom part
253: accommodated part
254: central concave part (supported part)
261: elastic part
262: engagement protrusion part
263: diameter variable part
2631: bottom part
264: central concave part
271: elastic part (energizing part)
272: bottom part
273: diameter variable part
281: female screw part
282: male screw part
283: top surface
284: knob part
300a, 300a', 300d, 300e, 300f: second engaging member
310: central convex part (support part)
311: passing hole
320, 320', 320a to 320d, 320a' to 320d': engagement receiving part
321, 321': side wall
322, 322': cover part
323, 323': bottom part 324: opening part
329: hollow part
340: male screw part
400: diameter variable body
410: connection part
411: folding part
420: upper part
430: lower part
O: rotation axis
SS: skin surface
X: needle-like member

What is claimed is:

1. A medical instrument comprising:
a medical device;
a sheet-shaped attaching member having an attachment surface that is attachable to a subject; and
a fixing tool fixing the medical device to the attaching member;
wherein the fixing tool comprises:
a first engaging member located on the medical device; and
a second engaging member located on a side of the attaching member opposite the attachment surface, the second engaging member being engageable with the first engaging member by rotation of the first engaging member with respect to the second engaging member;
wherein one of the first engaging member or the second engaging member comprises a plurality of engagement protrusion parts, each of which extends in a direction radially outward from a rotation axis of the first and second engaging members, and the other of the first engaging member or the second engaging member comprises a plurality of engagement receiving parts that are engageable with the plurality of engagement protrusion parts;
wherein the plurality of engagement protrusion parts includes a first engagement protrusion part and a second engagement protrusion part;
wherein the plurality of engagement receiving parts includes a first engagement receiving part that is engageable with the first engagement protrusion and a second engagement receiving part that is engageable with the second engagement protrusion part;
wherein a size and/or shape of the first engagement protrusion part is different from a size and/or shape of the second engagement protrusion part; and
wherein a size and/or shape of the first engagement receiving part is different from a size and/or shape of the second engagement receiving part.

2. The medical instrument according to claim 1, wherein:
the second engaging member comprises a support part located on the rotation axis and configured to support the first engaging member; and
the engagement receiving part is spaced apart from the support part.

3. The medical instrument according to claim 1, wherein:
the first engaging member comprises the plurality of engagement protrusion parts; and
at least one of the first and second engaging members comprises an energizing part provided separately from the plurality of engagement protrusion parts and the plurality of engagement receiving parts, the at least one of the first and second engaging members being configured to contract when pushed toward the other of the first engaging member or the second engaging member and to energize the plurality of engagement protrusion parts in a direction opposite to a direction in which the attaching member is positioned to thereby allow the plurality of engagement protrusion parts to come in contact with the plurality of engagement receiving parts.

4. The medical instrument according to claim 1, wherein:
the first engaging member includes the plurality of engagement protrusion parts and an energizing part connecting the plurality of engagement protrusion parts and the medical device to each other; and
the energizing part is configured to contract when pushed toward the second engaging member and to energize the plurality of engagement protrusion parts in a direction in which the attaching member is positioned to thereby allow the plurality of engagement protrusion parts to come in contact with the plurality of engagement receiving parts.

5. The medical instrument according to claim 1, wherein the plurality of engagement protrusion parts is configured to be formed by being pushed toward the other of the first engaging member or the second engaging member.

6. A medical instrument comprising:
a medical device;
a sheet-shaped attaching member having an attachment surface that is attachable to a subject; and
a fixing tool fixing the medical device to the attaching member;
wherein the fixing tool comprises:
a first engaging member located on the medical device; and
a second engaging member located on a side of the attaching member opposite the attachment surface, the second engaging member being engageable with the first engaging member by rotation of the first engaging member with respect to the second engaging member;
wherein one of the first engaging member or the second engaging member includes a male screw part, and the other of the first engaging member or the second engaging member includes a female screw part that is screwable with the male screw part.

* * * * *